US009376421B2

(12) United States Patent
Zimmerman et al.

(10) Patent No.: US 9,376,421 B2
(45) Date of Patent: Jun. 28, 2016

(54) COMPOUNDS AND METHODS FOR MYOTONIC DYSTROPHY THERAPY

(71) Applicant: The Board of Trustees of the University of Illinois, Urbana, IL (US)

(72) Inventors: Steven C. Zimmerman, Champaign, IL (US); Long M. Luu, Urbana, IL (US); Lien T. T. Nguyen, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/822,796

(22) Filed: Aug. 10, 2015

(65) Prior Publication Data

US 2016/0052914 A1  Feb. 25, 2016

Related U.S. Application Data

(60) Provisional application No. 62/034,932, filed on Aug. 8, 2014.

(51) Int. Cl.
| | |
|---|---|
| *A61K 31/53* | (2006.01) |
| *C07D 403/12* | (2006.01) |
| *C07D 401/12* | (2006.01) |
| *C07D 401/14* | (2006.01) |

(52) U.S. Cl.
CPC ............ *C07D 403/12* (2013.01); *C07D 401/12* (2013.01); *C07D 401/14* (2013.01)

(58) Field of Classification Search
CPC ..... A61K 31/53; C07D 403/00; C07D 403/12; C07D 401/12
USPC .......................................... 514/245; 544/198
See application file for complete search history.

(56) References Cited

U.S. PATENT DOCUMENTS

| | | | |
|---|---|---|---|
| 5,834,451 | A | 11/1998 | Ohsawa et al. |
| 6,987,123 | B2 | 1/2006 | Lohray et al. |

(Continued)

OTHER PUBLICATIONS

Jahromi et al, Nucleic Acids Research (2013), vol. 41(13), pp. 6687-6697.*

(Continued)

*Primary Examiner* — Kamal Saeed
*Assistant Examiner* — Janet L Coppins
(74) *Attorney, Agent, or Firm* — Haukaas Fortius PLLC; Michael Haukaas

(57) ABSTRACT

The invention provides rationally designed multi-targeting therapeutic agents for myotonic dystrophy type 1 (DM1), an incurable neuromuscular disease that originates in an abnormal expansion of CTG repeats ($CTG^{exp}$) in the DMPK gene. The rationally designed small molecules target the DM1 pathobiology in three distinct ways: (1) binding the expanded trinucleotide repeat, $CTG^{exp}$, and inhibiting its transcription to the toxic $CUG^{exp}$ RNA, (2) binding the $CUG^{exp}$ RNA and releasing sequestered muscleblind-like protein (MBNL1), and (3) cleaving the toxic $CUG^{exp}$ in an RNase-like manner. Importantly, the compounds can reduce the levels of $CUG^{exp}$ in DM1 model cells and reverse two separate $CUG^{exp}$-induced phenotypes of DM1.

20 Claims, 14 Drawing Sheets

(56) References Cited

U.S. PATENT DOCUMENTS

| | | |
|---|---|---|
| 7,589,123 B2 | 9/2009 | Rees et al. |
| 7,704,951 B2 | 4/2010 | Hirashima et al. |
| 8,754,084 B2 | 6/2014 | Zimmerman et al. |
| 2008/0227213 A1 | 9/2008 | Disney |
| 2010/0323993 A1 | 12/2010 | Berglund et al. |

OTHER PUBLICATIONS

Arambula, Jonathan F. et al., "A simple ligand that selectively targets CUG trinucleotide repeats and inhibits MBNL protein binding," PNAS, 2009, 16068-16073, 106.

David, Arnaud et al., "DNA Mismatch-Specific Base Flipping by a Bisacridine Macrocycle," ChemBioChem, 2003, 1326-1331, 4.

Gareiss, Peter C. et al., "Dynamic Combinatorial Selection of Molecules Capable of Inhibiting the (CUG) Repeat RNA-MBNL1 Interaction In Vitro: Discovery of Lead Compounds Targeting Myotonic Dystrophy(DM1)," JACS, 2008, 16254-16261, 130.

International Search Report dated Nov. 19, 2015; Application No. PCT/US15/044526 filed Aug. 10, 2015.

Jahromi, Amin H. et al., "A Novel CUGexp-MBNL1 Inhibitor with Therapeutic Potential for Myotonic Dystrophy Type 1," Chemical Biology, 2013, 1037-1043, 8.

Jahromi, Amin H. et al., "Developing Bivalent Ligands to Target CUG Triplet Repeats, the Causative Agent of Myotonic Dystrophy Type 1," Journal of Medicinal Chemistry, 2013, 9471-9481, 56.

Jahromi, Amin H. et al., "Single-molecule study of the CUG repeat—MBNL1 interaction and its inhibition by small molecules," Nucleic Acids Research, 2013, 6687-6697, 41.

Mooers, Blaine H. et al., "The structural basis of myotonic dystrophy from the crystal structure of CUG repeats," PNAS, 2005, 16626-16631, 102.

Wong, Chun-Ho et al., "Selective inhibition of MBNL1—CCUG interaction by small molecules toward potential terapeutic agents for myotonic dystrophy type 2 (DM2)," Nucleic Acids Research, 2011, 8881-8890, 39.

Wong, Chun-Ho et al., "Targeting Toxic RNAs that Cause Myotonic Dystrophy Type 1 (DM1) with a Bisamidinium Inhibitor," JACS, 2014, 6355-6361, 136.

Wong, Chun-Ho, "Discovery of Small Molecule Inhibitors of MBNL • RNA Interaction: Toward Therapeutic Agents to Treat Myotonic Dystrophy," The Chinese University of Hong Kong (Presentation), 2012, 9 pages.

Written Opinion dated Nov. 19, 2015; Application No. PCT/US15/044526 filed Aug. 10, 2015.

\* cited by examiner

*Fig. 1A-B*

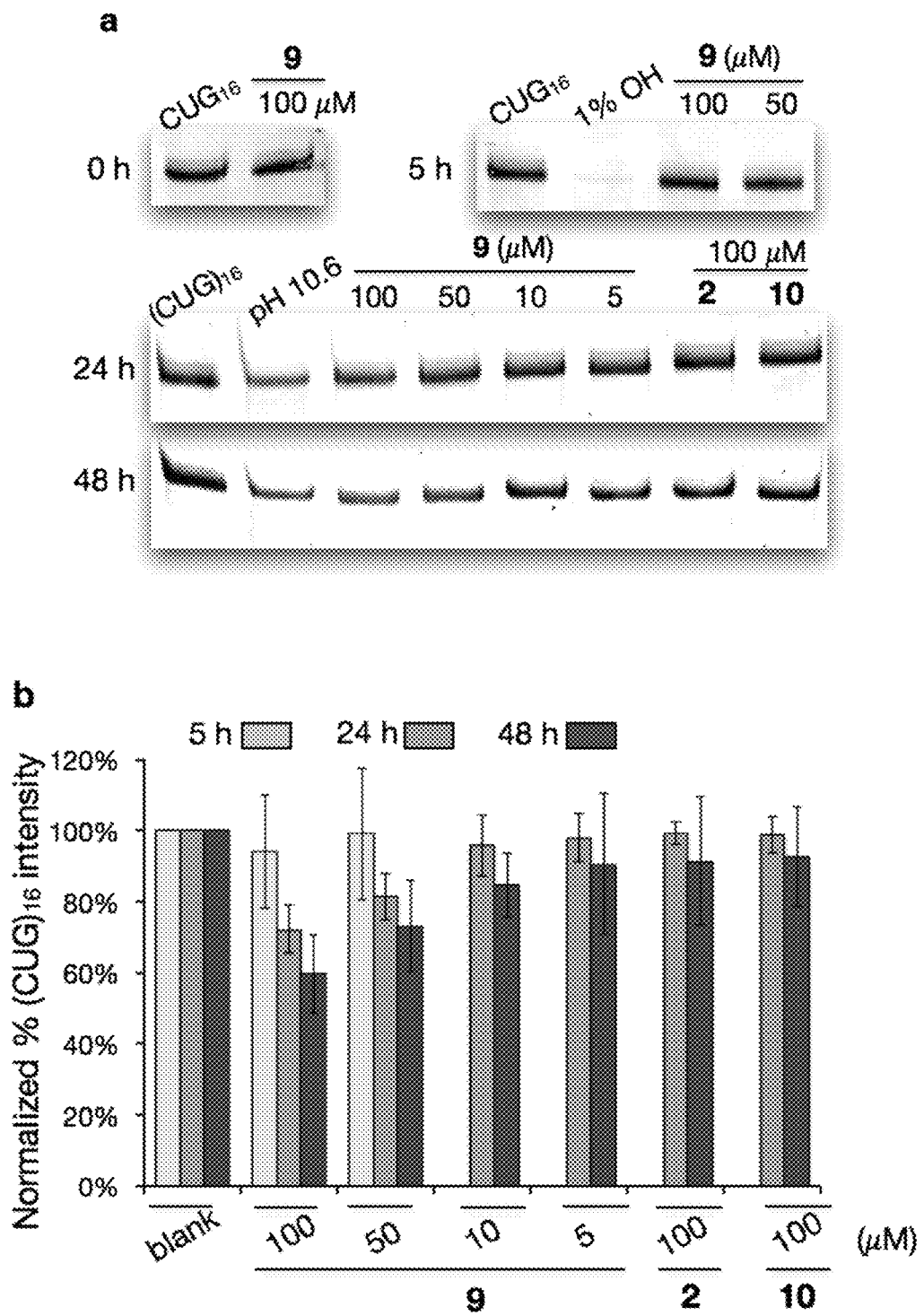
*Fig. 4A-B*

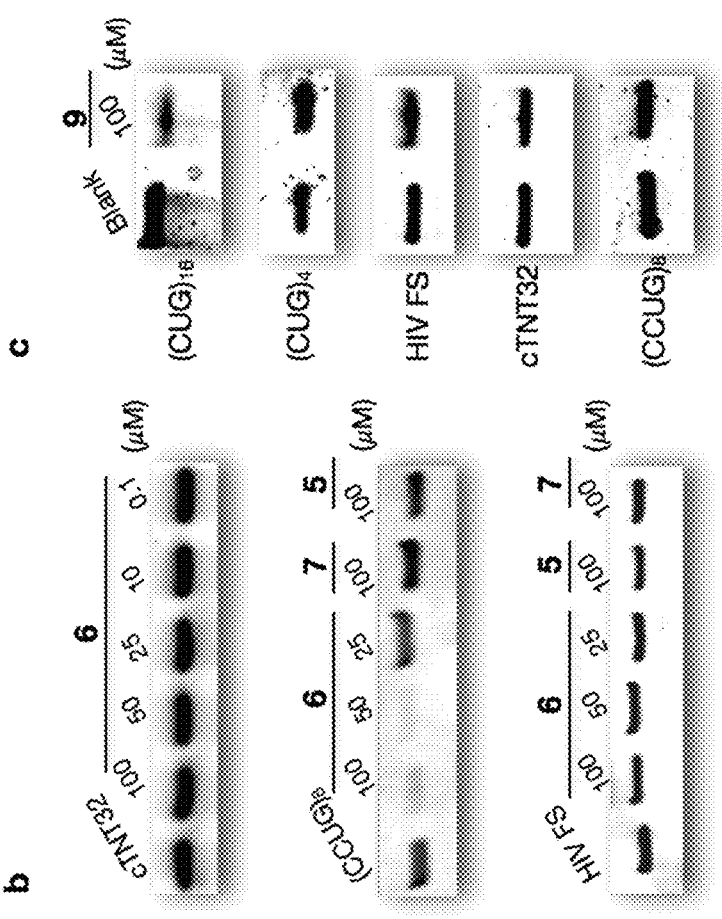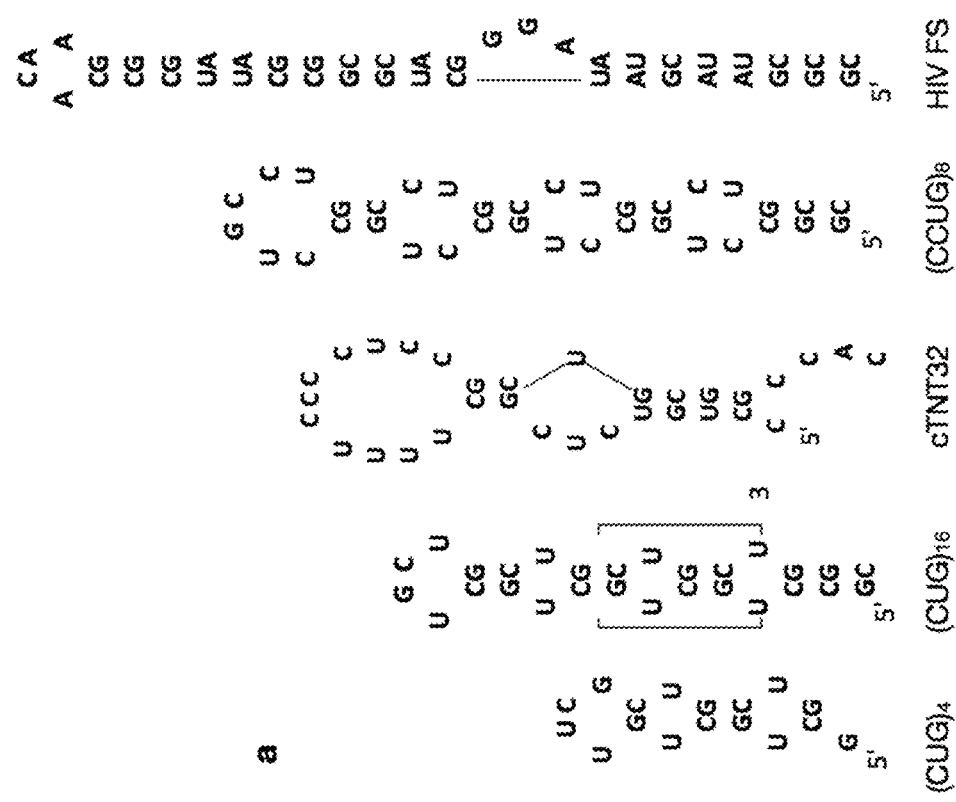
Fig. 5A-C

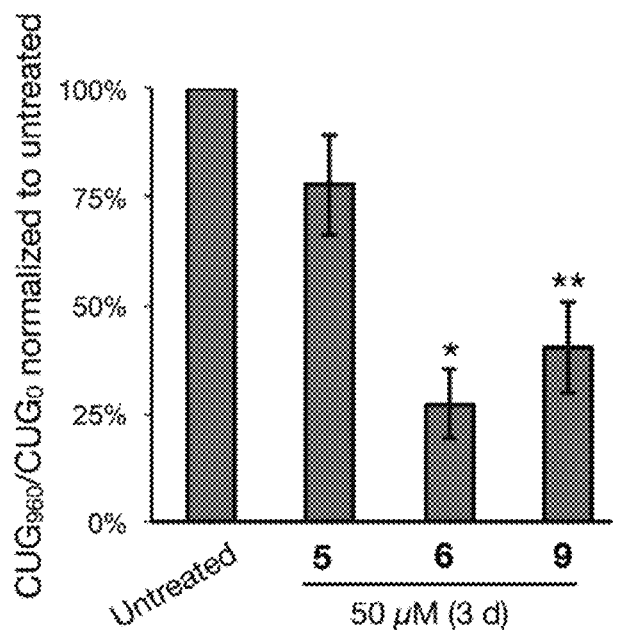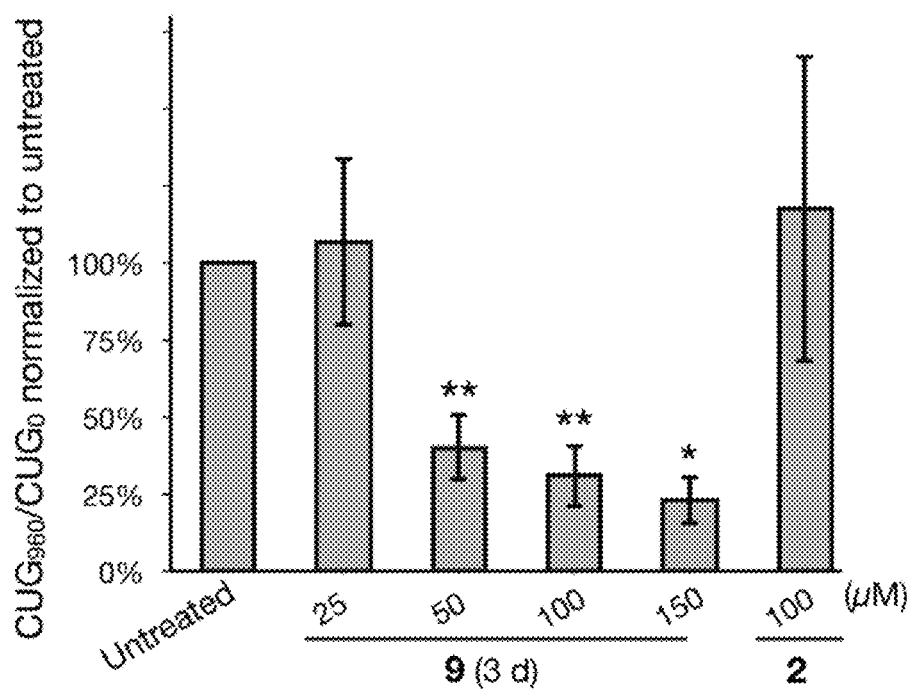
Fig. 7A-B

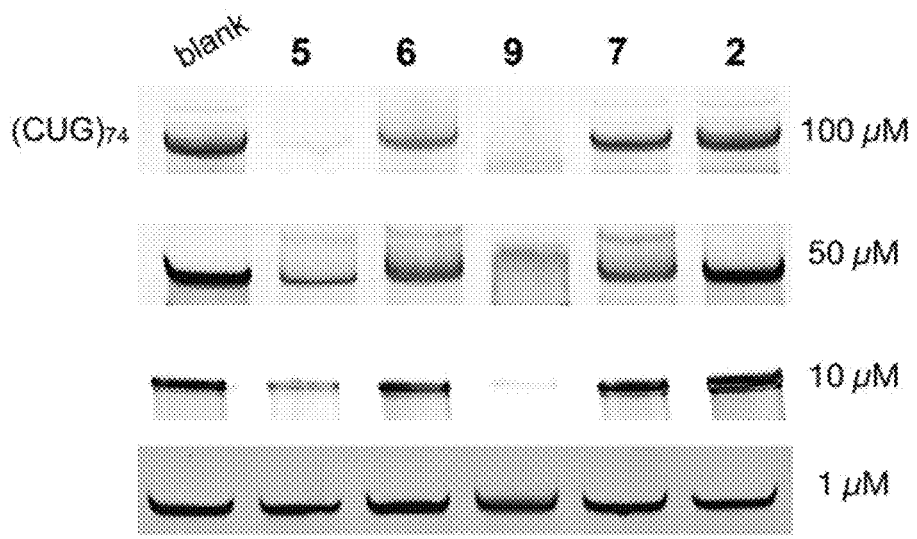
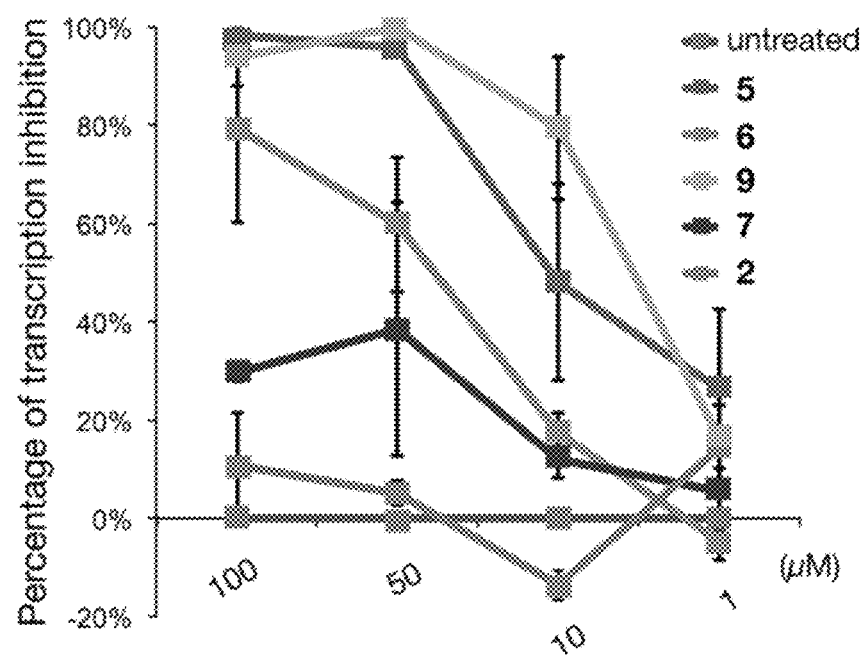
*Fig. 8A-B*

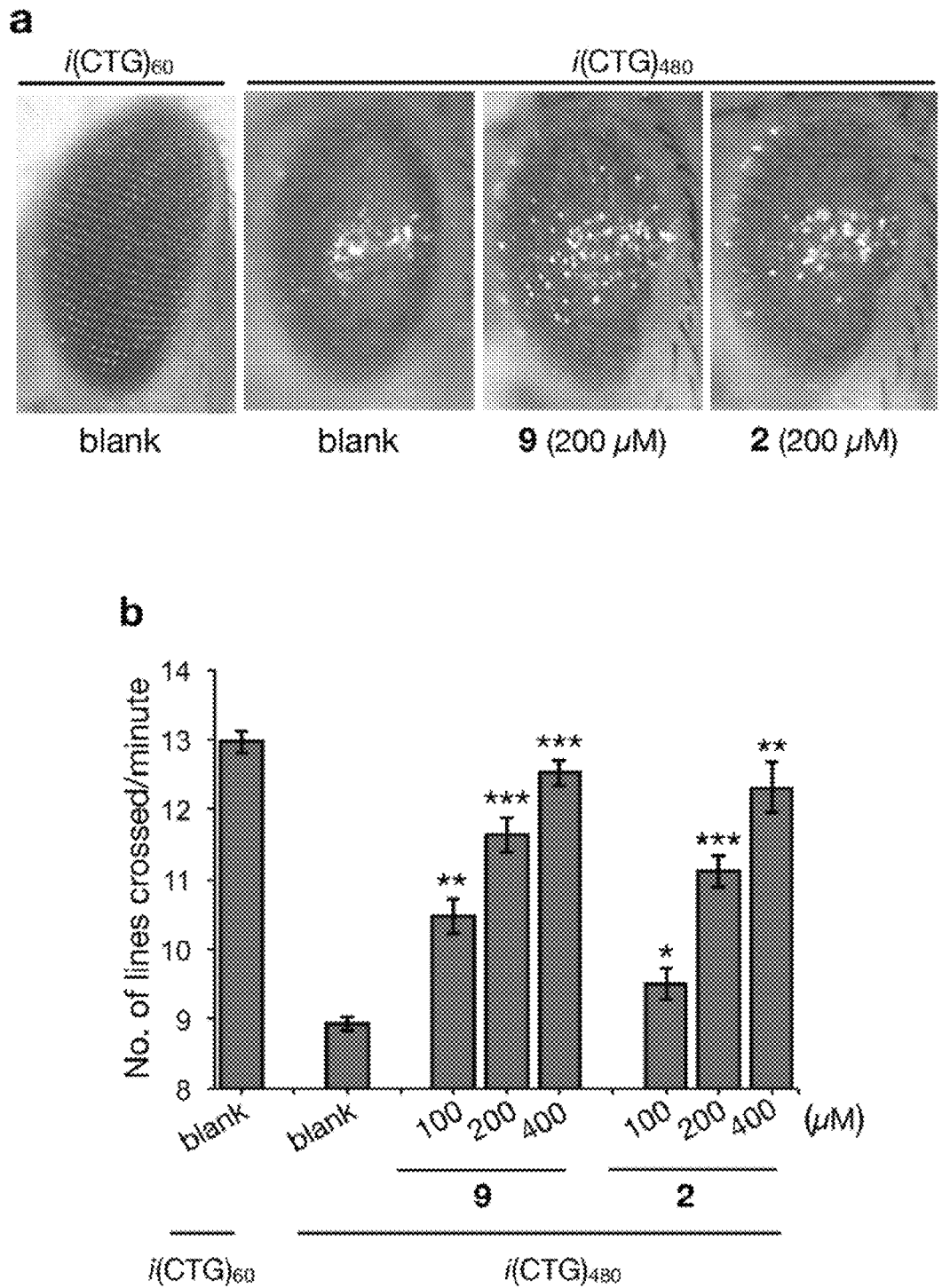
Fig. 9A-B c
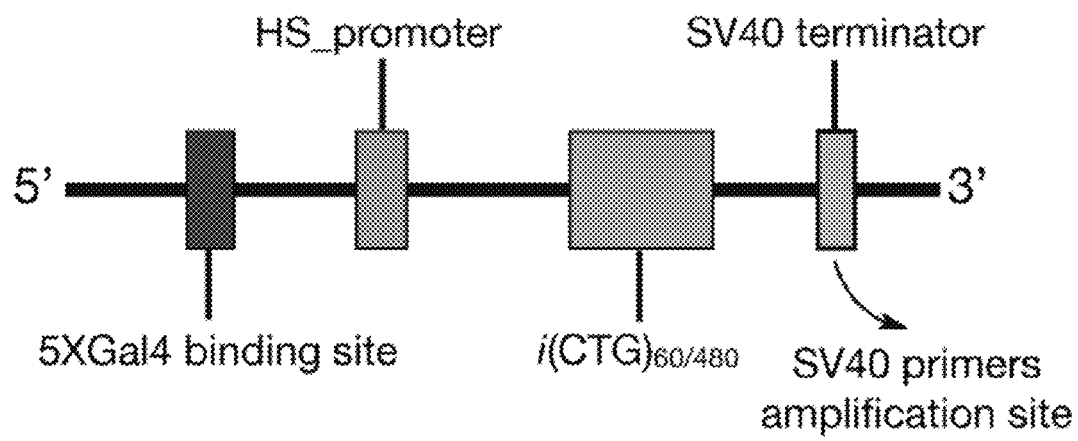
d
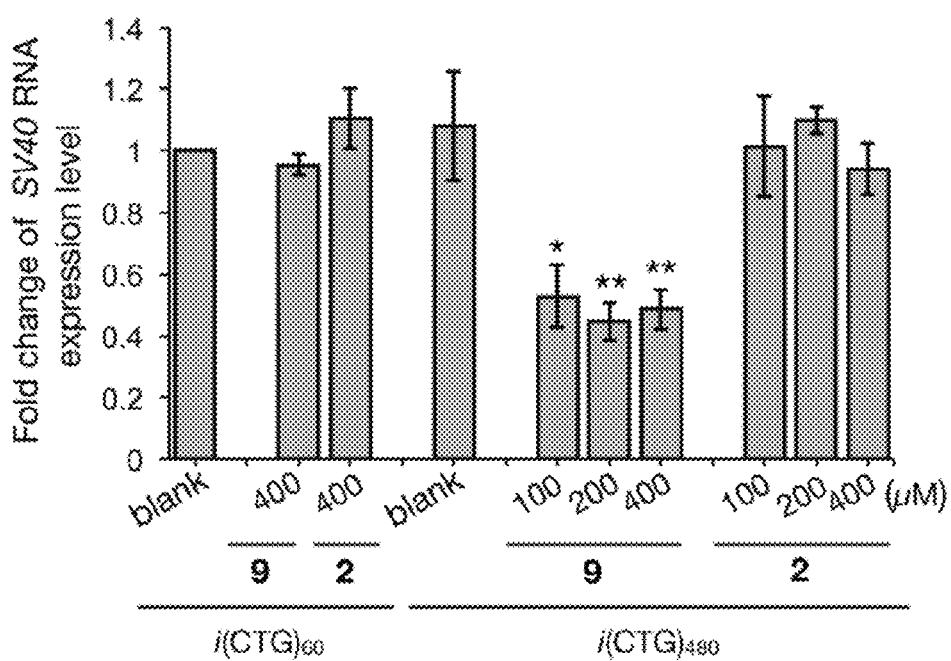
*Fig. 9C-D*

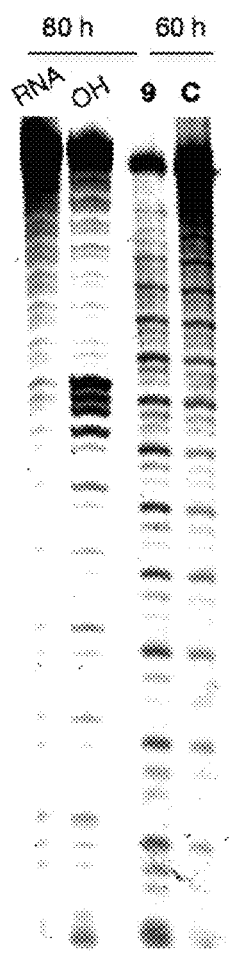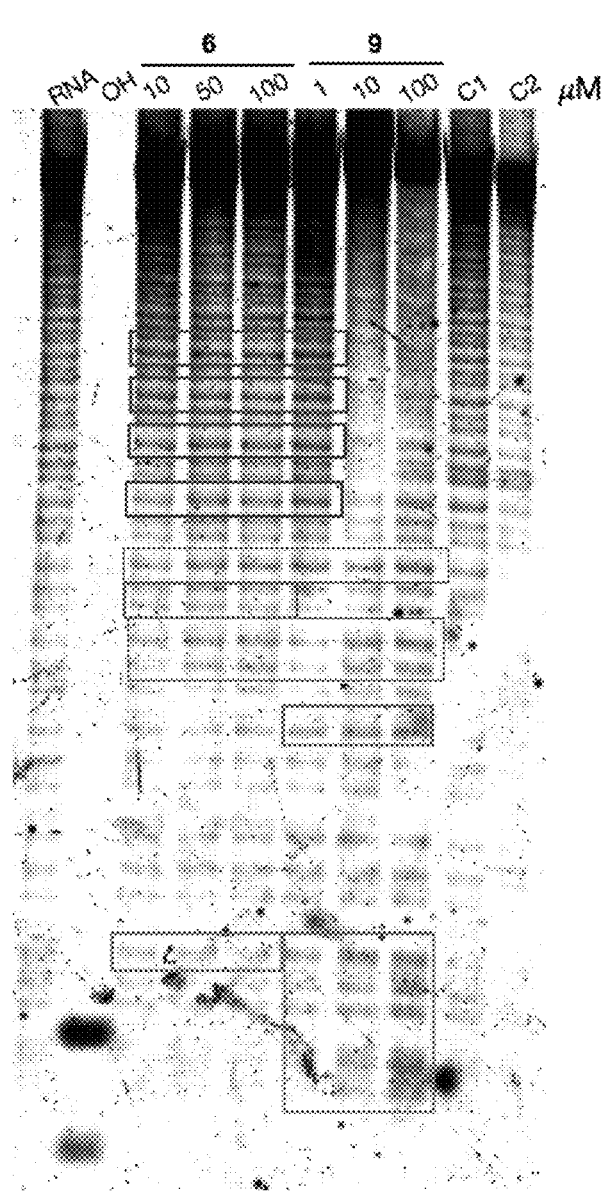
Fig. 10A-B

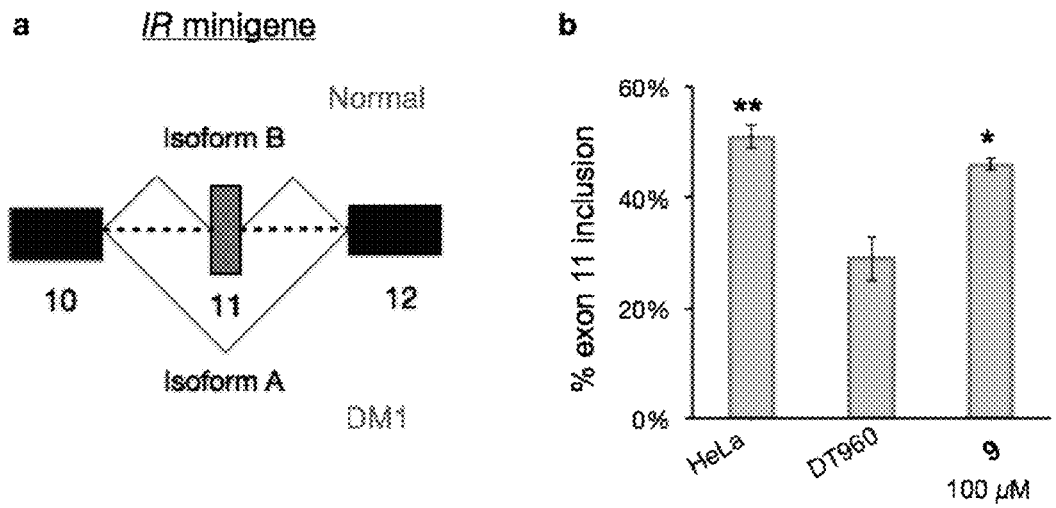
Fig. 11A-B
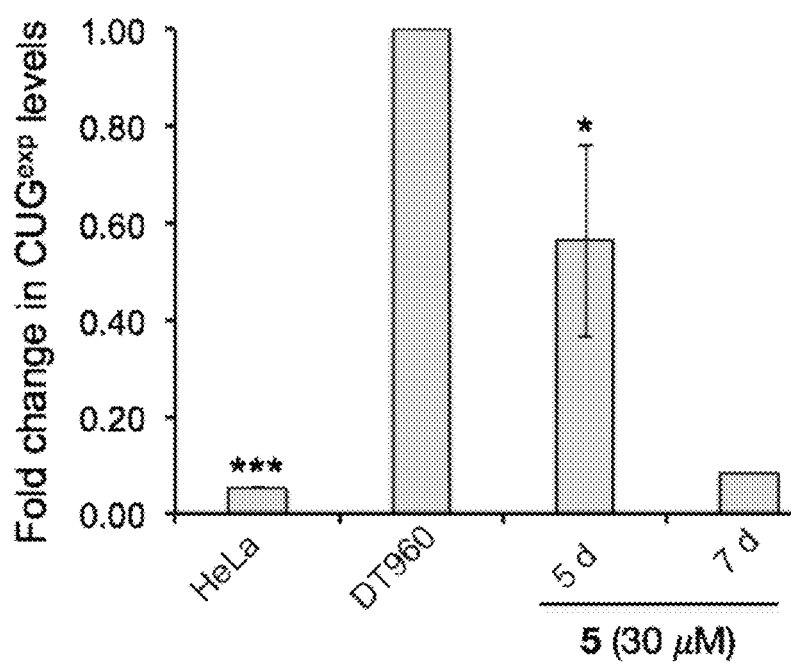
Fig. 12

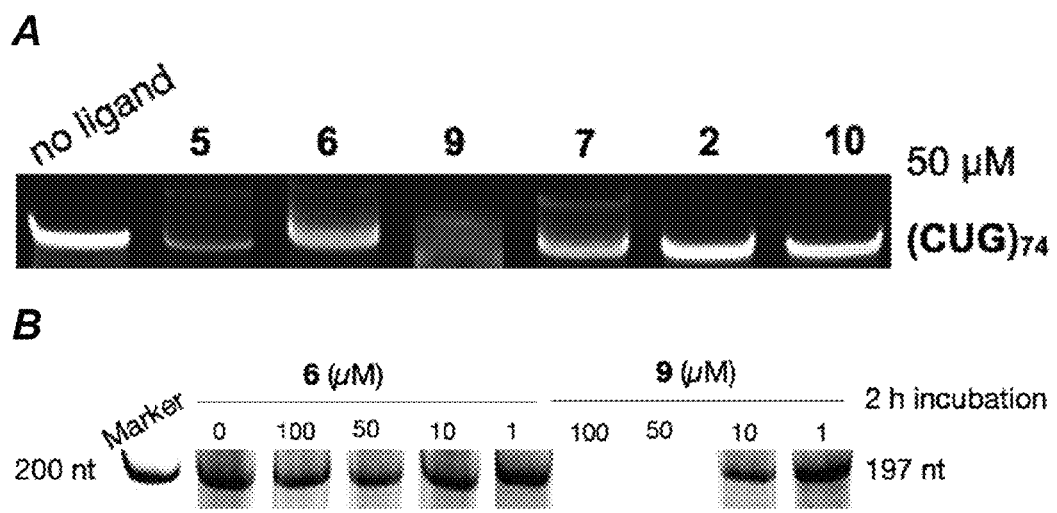
*Fig. 13A-B*
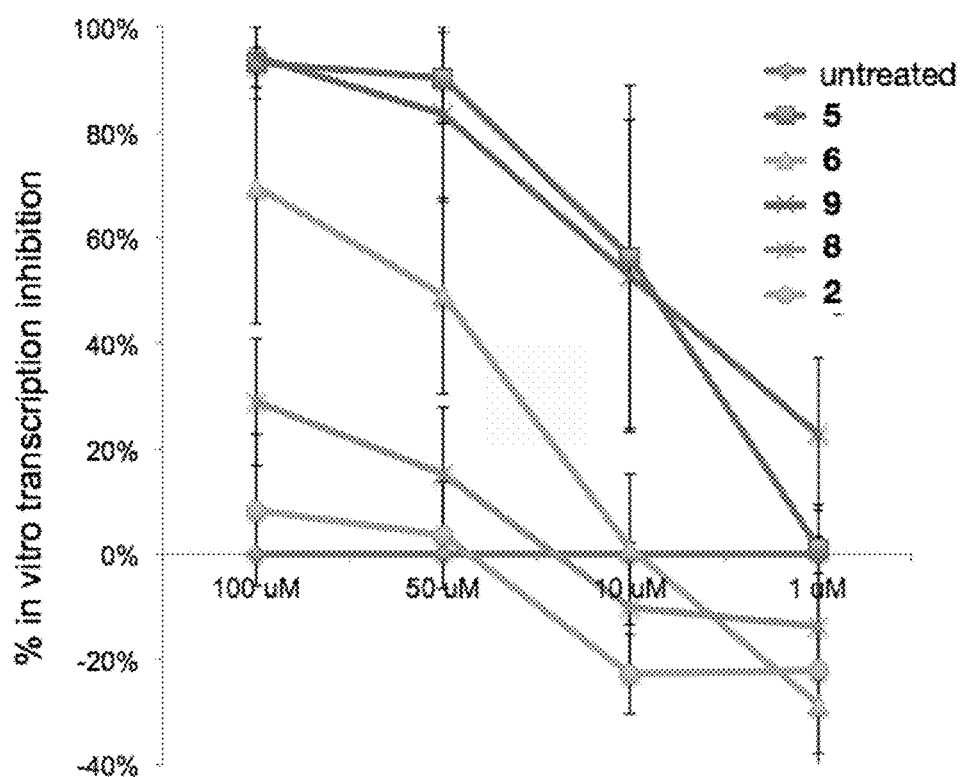
*Fig. 14*

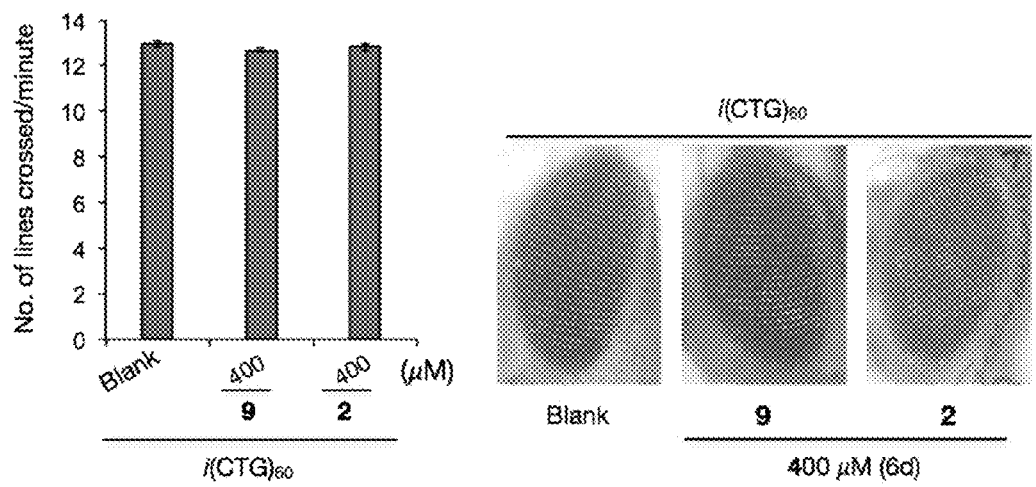
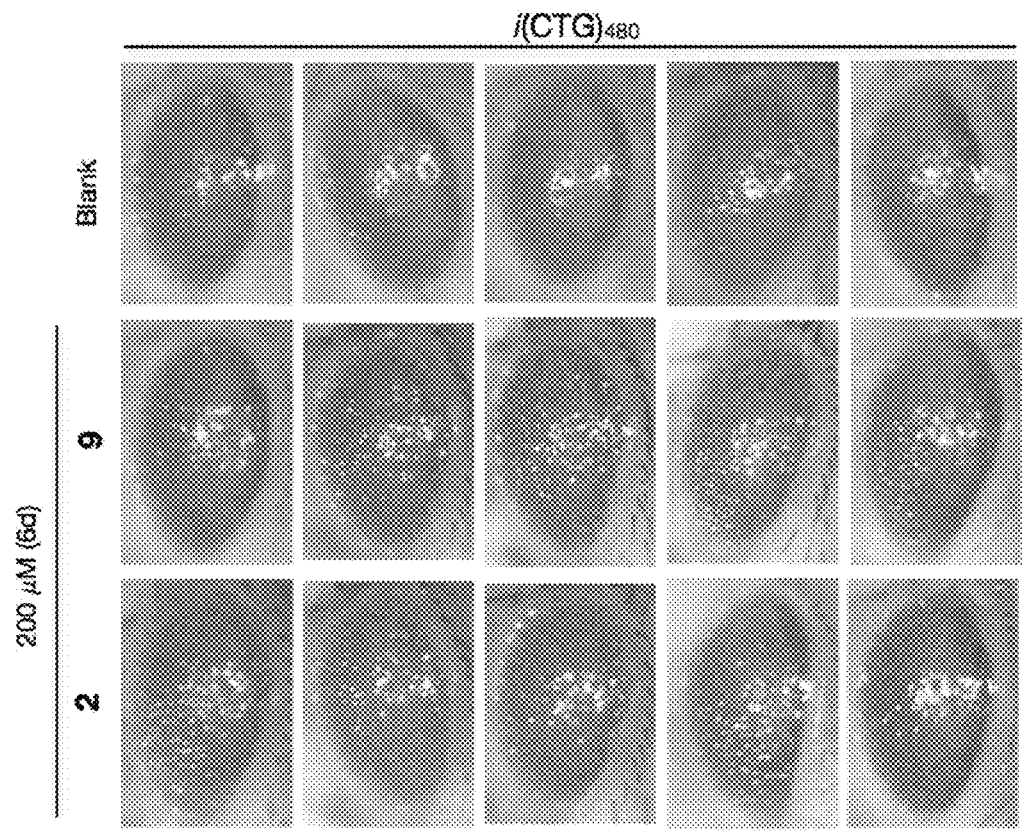
*Fig. 15A-B*

```
                         SEQUENCE LISTING

<160> NUMBER OF SEQ ID NOS: 32

<210> SEQ ID NO 1
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cugcugcugc ugcugcugcu gcugcugcug cugcugcugc ugcugcug            48

<210> SEQ ID NO 2
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cagcagcagc agcagcagca gcagcagcag                                30

<210> SEQ ID NO 3
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ctgctgctgc tgctgctgct gctgctgctg ctgctgctgc tgctgctgct gctgctgctg     60
ctgctgctgc tgctgctgct gctgctgctg ctgctgctgc tgctgctgct gctgctgctg    120
ctgctgctgc tgctgctgct gctgctgctg ctgctgctgc tgctgctgct gctgctgctg    180
ctgctgctgc tgctgctgct gctgctgctg ctgctgctgc tg                       222

<210> SEQ ID NO 4
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc ag                       222

<210> SEQ ID NO 5
<211> LENGTH: 180
<212> TYPE: DNA
<213> ORGANISM: Artificial Sequence
```

<220> FEATURE:
<223> OTHER INFORMATION: Description of Artificial Sequence: Synthetic
     polynucleotide

<400> SEQUENCE: 5

```
ctgctgctgc tgctgctgct gctgctgctg ctgctgctgc tgctgctgct gctgctgctg      60
ctgctgctgc tgctgctgct gctgctgctg ctgctgctgc tgctgctgct gctgctgctg     120
ctgctgctgc tgctgctgct gctgctgctg ctgctgctgc tgctgctgct gctgctgctg     180
```

<210> SEQ ID NO 6
<211> LENGTH: 1440
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 6

```
ctgctgctgc tgctgctgct gctgctgctg ctgctgctgc tgctgctgct gctgctgctg      60
ctgctgctgc tgctgctgct gctgctgctg ctgctgctgc tgctgctgct gctgctgctg     120
ctgctgctgc tgctgctgct gctgctgctg ctgctgctgc tgctgctgct gctgctgctg     180
ctgctgctgc tgctgctgct gctgctgctg ctgctgctgc tgctgctgct gctgctgctg     240
ctgctgctgc tgctgctgct gctgctgctg ctgctgctgc tgctgctgct gctgctgctg     300
ctgctgctgc tgctgctgct gctgctgctg ctgctgctgc tgctgctgct gctgctgctg     360
ctgctgctgc tgctgctgct gctgctgctg ctgctgctgc tgctgctgct gctgctgctg     420
ctgctgctgc tgctgctgct gctgctgctg ctgctgctgc tgctgctgct gctgctgctg     480
ctgctgctgc tgctgctgct gctgctgctg ctgctgctgc tgctgctgct gctgctgctg     540
ctgctgctgc tgctgctgct gctgctgctg ctgctgctgc tgctgctgct gctgctgctg     600
ctgctgctgc tgctgctgct gctgctgctg ctgctgctgc tgctgctgct gctgctgctg     660
ctgctgctgc tgctgctgct gctgctgctg ctgctgctgc tgctgctgct gctgctgctg     720
ctgctgctgc tgctgctgct gctgctgctg ctgctgctgc tgctgctgct gctgctgctg     780
ctgctgctgc tgctgctgct gctgctgctg ctgctgctgc tgctgctgct gctgctgctg     840
ctgctgctgc tgctgctgct gctgctgctg ctgctgctgc tgctgctgct gctgctgctg     900
ctgctgctgc tgctgctgct gctgctgctg ctgctgctgc tgctgctgct gctgctgctg     960
ctgctgctgc tgctgctgct gctgctgctg ctgctgctgc tgctgctgct gctgctgctg    1020
ctgctgctgc tgctgctgct gctgctgctg ctgctgctgc tgctgctgct gctgctgctg    1080
ctgctgctgc tgctgctgct gctgctgctg ctgctgctgc tgctgctgct gctgctgctg    1140
ctgctgctgc tgctgctgct gctgctgctg ctgctgctgc tgctgctgct gctgctgctg    1200
ctgctgctgc tgctgctgct gctgctgctg ctgctgctgc tgctgctgct gctgctgctg    1260
ctgctgctgc tgctgctgct gctgctgctg ctgctgctgc tgctgctgct gctgctgctg    1320
ctgctgctgc tgctgctgct gctgctgctg ctgctgctgc tgctgctgct gctgctgctg    1380
ctgctgctgc tgctgctgct gctgctgctg ctgctgctgc tgctgctgct gctgctgctg    1440
```

<210> SEQ ID NO 7
<211> LENGTH: 2880
<212> TYPE: RNA
<213> ORGANISM: Artificial Sequence
<220> FEATURE:
<223> OTHER INFORMATION: Description of Artificial Sequence: Synthetic
     polynucleotide

<400> SEQUENCE: 7

| | | | | | |
|---|---|---|---|---|---|
| cugcugcugc | ugcugcugcu | gcugcugcug | cugcugcugc | ugcugcugcu | gcugcugcug | 60 |
| cugcugcugc | ugcugcugcu | gcugcugcug | cugcugcugc | ugcugcugcu | gcugcugcug | 120 |
| cugcugcugc | ugcugcugcu | gcugcugcug | cugcugcugc | ugcugcugcu | gcugcugcug | 180 |
| cugcugcugc | ugcugcugcu | gcugcugcug | cugcugcugc | ugcugcugcu | gcugcugcug | 240 |
| cugcugcugc | ugcugcugcu | gcugcugcug | cugcugcugc | ugcugcugcu | gcugcugcug | 300 |
| cugcugcugc | ugcugcugcu | gcugcugcug | cugcugcugc | ugcugcugcu | gcugcugcug | 360 |
| cugcugcugc | ugcugcugcu | gcugcugcug | cugcugcugc | ugcugcugcu | gcugcugcug | 420 |
| cugcugcugc | ugcugcugcu | gcugcugcug | cugcugcugc | ugcugcugcu | gcugcugcug | 480 |
| cugcugcugc | ugcugcugcu | gcugcugcug | cugcugcugc | ugcugcugcu | gcugcugcug | 540 |
| cugcugcugc | ugcugcugcu | gcugcugcug | cugcugcugc | ugcugcugcu | gcugcugcug | 600 |
| cugcugcugc | ugcugcugcu | gcugcugcug | cugcugcugc | ugcugcugcu | gcugcugcug | 660 |
| cugcugcugc | ugcugcugcu | gcugcugcug | cugcugcugc | ugcugcugcu | gcugcugcug | 720 |
| cugcugcugc | ugcugcugcu | gcugcugcug | cugcugcugc | ugcugcugcu | gcugcugcug | 780 |
| cugcugcugc | ugcugcugcu | gcugcugcug | cugcugcugc | ugcugcugcu | gcugcugcug | 840 |
| cugcugcugc | ugcugcugcu | gcugcugcug | cugcugcugc | ugcugcugcu | gcugcugcug | 900 |
| cugcugcugc | ugcugcugcu | gcugcugcug | cugcugcugc | ugcugcugcu | gcugcugcug | 960 |
| cugcugcugc | ugcugcugcu | gcugcugcug | cugcugcugc | ugcugcugcu | gcugcugcug | 1020 |
| cugcugcugc | ugcugcugcu | gcugcugcug | cugcugcugc | ugcugcugcu | gcugcugcug | 1080 |
| cugcugcugc | ugcugcugcu | gcugcugcug | cugcugcugc | ugcugcugcu | gcugcugcug | 1140 |
| cugcugcugc | ugcugcugcu | gcugcugcug | cugcugcugc | ugcugcugcu | gcugcugcug | 1200 |
| cugcugcugc | ugcugcugcu | gcugcugcug | cugcugcugc | ugcugcugcu | gcugcugcug | 1260 |
| cugcugcugc | ugcugcugcu | gcugcugcug | cugcugcugc | ugcugcugcu | gcugcugcug | 1320 |
| cugcugcugc | ugcugcugcu | gcugcugcug | cugcugcugc | ugcugcugcu | gcugcugcug | 1380 |
| cugcugcugc | ugcugcugcu | gcugcugcug | cugcugcugc | ugcugcugcu | gcugcugcug | 1440 |
| cugcugcugc | ugcugcugcu | gcugcugcug | cugcugcugc | ugcugcugcu | gcugcugcug | 1500 |
| cugcugcugc | ugcugcugcu | gcugcugcug | cugcugcugc | ugcugcugcu | gcugcugcug | 1560 |
| cugcugcugc | ugcugcugcu | gcugcugcug | cugcugcugc | ugcugcugcu | gcugcugcug | 1620 |
| cugcugcugc | ugcugcugcu | gcugcugcug | cugcugcugc | ugcugcugcu | gcugcugcug | 1680 |
| cugcugcugc | ugcugcugcu | gcugcugcug | cugcugcugc | ugcugcugcu | gcugcugcug | 1740 |
| cugcugcugc | ugcugcugcu | gcugcugcug | cugcugcugc | ugcugcugcu | gcugcugcug | 1800 |
| cugcugcugc | ugcugcugcu | gcugcugcug | cugcugcugc | ugcugcugcu | gcugcugcug | 1860 |
| cugcugcugc | ugcugcugcu | gcugcugcug | cugcugcugc | ugcugcugcu | gcugcugcug | 1920 |
| cugcugcugc | ugcugcugcu | gcugcugcug | cugcugcugc | ugcugcugcu | gcugcugcug | 1980 |
| cugcugcugc | ugcugcugcu | gcugcugcug | cugcugcugc | ugcugcugcu | gcugcugcug | 2040 |
| cugcugcugc | ugcugcugcu | gcugcugcug | cugcugcugc | ugcugcugcu | gcugcugcug | 2100 |
| cugcugcugc | ugcugcugcu | gcugcugcug | cugcugcugc | ugcugcugcu | gcugcugcug | 2160 |
| cugcugcugc | ugcugcugcu | gcugcugcug | cugcugcugc | ugcugcugcu | gcugcugcug | 2220 |
| cugcugcugc | ugcugcugcu | gcugcugcug | cugcugcugc | ugcugcugcu | gcugcugcug | 2280 |

```
cugcugcugc ugcugcugcu gcugcugcug cugcugcugc ugcugcugcu gcugcugcug    2340
cugcugcugc ugcugcugcu gcugcugcug cugcugcugc ugcugcugcu gcugcugcug    2400
cugcugcugc ugcugcugcu gcugcugcug cugcugcugc ugcugcugcu gcugcugcug    2460
cugcugcugc ugcugcugcu gcugcugcug cugcugcugc ugcugcugcu gcugcugcug    2520
cugcugcugc ugcugcugcu gcugcugcug cugcugcugc ugcugcugcu gcugcugcug    2580
cugcugcugc ugcugcugcu gcugcugcug cugcugcugc ugcugcugcu gcugcugcug    2640
cugcugcugc ugcugcugcu gcugcugcug cugcugcugc ugcugcugcu gcugcugcug    2700
cugcugcugc ugcugcugcu gcugcugcug cugcugcugc ugcugcugcu gcugcugcug    2760
cugcugcugc ugcugcugcu gcugcugcug cugcugcugc ugcugcugcu gcugcugcug    2820
cugcugcugc ugcugcugcu gcugcugcug cugcugcugc ugcugcugcu gcugcugcug    2880
```

<210> SEQ ID NO 8
<211> LENGTH: 180
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8

```
cugcugcugc ugcugcugcu gcugcugcug cugcugcugc ugcugcugcu gcugcugcug      60
cugcugcugc ugcugcugcu gcugcugcug cugcugcugc ugcugcugcu gcugcugcug     120
cugcugcugc ugcugcugcu gcugcugcug cugcugcugc ugcugcugcu gcugcugcug     180
```

<210> SEQ ID NO 9
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

```
cugcugcugc ugcugcug                                                    18
```

<210> SEQ ID NO 10
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cugcugcugc ug                                                          12
```

<210> SEQ ID NO 11
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ccugccugcc ugccugccug ccugccugcc ug                                    32
```

<210> SEQ ID NO 12
<211> LENGTH: 24

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12
ccugccugcc ugccugccug ccug                                              24

<210> SEQ ID NO 13
<211> LENGTH: 2880
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
ctgctgctgc tgctgctgct gctgctgctg ctgctgctgc tgctgctgct gctgctgctg      60
ctgctgctgc tgctgctgct gctgctgctg ctgctgctgc tgctgctgct gctgctgctg     120
ctgctgctgc tgctgctgct gctgctgctg ctgctgctgc tgctgctgct gctgctgctg     180
ctgctgctgc tgctgctgct gctgctgctg ctgctgctgc tgctgctgct gctgctgctg     240
ctgctgctgc tgctgctgct gctgctgctg ctgctgctgc tgctgctgct gctgctgctg     300
ctgctgctgc tgctgctgct gctgctgctg ctgctgctgc tgctgctgct gctgctgctg     360
ctgctgctgc tgctgctgct gctgctgctg ctgctgctgc tgctgctgct gctgctgctg     420
ctgctgctgc tgctgctgct gctgctgctg ctgctgctgc tgctgctgct gctgctgctg     480
ctgctgctgc tgctgctgct gctgctgctg ctgctgctgc tgctgctgct gctgctgctg     540
ctgctgctgc tgctgctgct gctgctgctg ctgctgctgc tgctgctgct gctgctgctg     600
ctgctgctgc tgctgctgct gctgctgctg ctgctgctgc tgctgctgct gctgctgctg     660
ctgctgctgc tgctgctgct gctgctgctg ctgctgctgc tgctgctgct gctgctgctg     720
ctgctgctgc tgctgctgct gctgctgctg ctgctgctgc tgctgctgct gctgctgctg     780
ctgctgctgc tgctgctgct gctgctgctg ctgctgctgc tgctgctgct gctgctgctg     840
ctgctgctgc tgctgctgct gctgctgctg ctgctgctgc tgctgctgct gctgctgctg     900
ctgctgctgc tgctgctgct gctgctgctg ctgctgctgc tgctgctgct gctgctgctg     960
ctgctgctgc tgctgctgct gctgctgctg ctgctgctgc tgctgctgct gctgctgctg    1020
ctgctgctgc tgctgctgct gctgctgctg ctgctgctgc tgctgctgct gctgctgctg    1080
ctgctgctgc tgctgctgct gctgctgctg ctgctgctgc tgctgctgct gctgctgctg    1140
ctgctgctgc tgctgctgct gctgctgctg ctgctgctgc tgctgctgct gctgctgctg    1200
ctgctgctgc tgctgctgct gctgctgctg ctgctgctgc tgctgctgct gctgctgctg    1260
ctgctgctgc tgctgctgct gctgctgctg ctgctgctgc tgctgctgct gctgctgctg    1320
ctgctgctgc tgctgctgct gctgctgctg ctgctgctgc tgctgctgct gctgctgctg    1380
ctgctgctgc tgctgctgct gctgctgctg ctgctgctgc tgctgctgct gctgctgctg    1440
ctgctgctgc tgctgctgct gctgctgctg ctgctgctgc tgctgctgct gctgctgctg    1500
ctgctgctgc tgctgctgct gctgctgctg ctgctgctgc tgctgctgct gctgctgctg    1560
ctgctgctgc tgctgctgct gctgctgctg ctgctgctgc tgctgctgct gctgctgctg    1620
ctgctgctgc tgctgctgct gctgctgctg ctgctgctgc tgctgctgct gctgctgctg    1680
ctgctgctgc tgctgctgct gctgctgctg ctgctgctgc tgctgctgct gctgctgctg    1740

-continued

```
ctgctgctgc tgctgctgct gctgctgctg ctgctgctgc tgctgctgct gctgctgctg     1800
ctgctgctgc tgctgctgct gctgctgctg ctgctgctgc tgctgctgct gctgctgctg     1860
ctgctgctgc tgctgctgct gctgctgctg ctgctgctgc tgctgctgct gctgctgctg     1920
ctgctgctgc tgctgctgct gctgctgctg ctgctgctgc tgctgctgct gctgctgctg     1980
ctgctgctgc tgctgctgct gctgctgctg ctgctgctgc tgctgctgct gctgctgctg     2040
ctgctgctgc tgctgctgct gctgctgctg ctgctgctgc tgctgctgct gctgctgctg     2100
ctgctgctgc tgctgctgct gctgctgctg ctgctgctgc tgctgctgct gctgctgctg     2160
ctgctgctgc tgctgctgct gctgctgctg ctgctgctgc tgctgctgct gctgctgctg     2220
ctgctgctgc tgctgctgct gctgctgctg ctgctgctgc tgctgctgct gctgctgctg     2280
ctgctgctgc tgctgctgct gctgctgctg ctgctgctgc tgctgctgct gctgctgctg     2340
ctgctgctgc tgctgctgct gctgctgctg ctgctgctgc tgctgctgct gctgctgctg     2400
ctgctgctgc tgctgctgct gctgctgctg ctgctgctgc tgctgctgct gctgctgctg     2460
ctgctgctgc tgctgctgct gctgctgctg ctgctgctgc tgctgctgct gctgctgctg     2520
ctgctgctgc tgctgctgct gctgctgctg ctgctgctgc tgctgctgct gctgctgctg     2580
ctgctgctgc tgctgctgct gctgctgctg ctgctgctgc tgctgctgct gctgctgctg     2640
ctgctgctgc tgctgctgct gctgctgctg ctgctgctgc tgctgctgct gctgctgctg     2700
ctgctgctgc tgctgctgct gctgctgctg ctgctgctgc tgctgctgct gctgctgctg     2760
ctgctgctgc tgctgctgct gctgctgctg ctgctgctgc tgctgctgct gctgctgctg     2820
ctgctgctgc tgctgctgct gctgctgctg ctgctgctgc tgctgctgct gctgctgctg     2880

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgctgctgc tgctgctgct gctgctgctg ctgctg                                36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcagcagc agcagcagca gcagcagcag cagcag                                36

<210> SEQ ID NO 16
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cugcugcugc ugcugcugcu gcugcugcug cugcug                                36

<210> SEQ ID NO 17
```

```
<211> LENGTH: 1440
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 17
cugcugcugc ugcugcugcu gcugcugcug cugcugcugc ugcugcugcu gcugcugcug      60
cugcugcugc ugcugcugcu gcugcugcug cugcugcugc ugcugcugcu gcugcugcug     120
cugcugcugc ugcugcugcu gcugcugcug cugcugcugc ugcugcugcu gcugcugcug     180
cugcugcugc ugcugcugcu gcugcugcug cugcugcugc ugcugcugcu gcugcugcug     240
cugcugcugc ugcugcugcu gcugcugcug cugcugcugc ugcugcugcu gcugcugcug     300
cugcugcugc ugcugcugcu gcugcugcug cugcugcugc ugcugcugcu gcugcugcug     360
cugcugcugc ugcugcugcu gcugcugcug cugcugcugc ugcugcugcu gcugcugcug     420
cugcugcugc ugcugcugcu gcugcugcug cugcugcugc ugcugcugcu gcugcugcug     480
cugcugcugc ugcugcugcu gcugcugcug cugcugcugc ugcugcugcu gcugcugcug     540
cugcugcugc ugcugcugcu gcugcugcug cugcugcugc ugcugcugcu gcugcugcug     600
cugcugcugc ugcugcugcu gcugcugcug cugcugcugc ugcugcugcu gcugcugcug     660
cugcugcugc ugcugcugcu gcugcugcug cugcugcugc ugcugcugcu gcugcugcug     720
cugcugcugc ugcugcugcu gcugcugcug cugcugcugc ugcugcugcu gcugcugcug     780
cugcugcugc ugcugcugcu gcugcugcug cugcugcugc ugcugcugcu gcugcugcug     840
cugcugcugc ugcugcugcu gcugcugcug cugcugcugc ugcugcugcu gcugcugcug     900
cugcugcugc ugcugcugcu gcugcugcug cugcugcugc ugcugcugcu gcugcugcug     960
cugcugcugc ugcugcugcu gcugcugcug cugcugcugc ugcugcugcu gcugcugcug    1020
cugcugcugc ugcugcugcu gcugcugcug cugcugcugc ugcugcugcu gcugcugcug    1080
cugcugcugc ugcugcugcu gcugcugcug cugcugcugc ugcugcugcu gcugcugcug    1140
cugcugcugc ugcugcugcu gcugcugcug cugcugcugc ugcugcugcu gcugcugcug    1200
cugcugcugc ugcugcugcu gcugcugcug cugcugcugc ugcugcugcu gcugcugcug    1260
cugcugcugc ugcugcugcu gcugcugcug cugcugcugc ugcugcugcu gcugcugcug    1320
cugcugcugc ugcugcugcu gcugcugcug cugcugcugc ugcugcugcu gcugcugcug    1380
cugcugcugc ugcugcugcu gcugcugcug cugcugcugc ugcugcugcu gcugcugcug    1440

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcggagcggt tgtgaact                                                    18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 19
gttcgccgtt gttctgtc                                                18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgctgttca tgtgcaaggt                                              20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caacagcatg ccagtgatt                                               19

<210> SEQ ID NO 22
<211> LENGTH: 222
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 22
cugcugcugc ugcugcugcu gcugcugcug cugcugcugc ugcugcugcu gcugcugcug    60
cugcugcugc ugcugcugcu gcugcugcug cugcugcugc ugcugcugcu gcugcugcug   120
cugcugcugc ugcugcugcu gcugcugcug cugcugcugc ugcugcugcu gcugcugcug   180
cugcugcugc ugcugcugcu gcugcugcug cugcugcugc ug                      222

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaagtcct tggggtcttc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaactgatg aatgggagca                                              20

<210> SEQ ID NO 25
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 25
atgtgcaagg ccggtttcgc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgacacgcag ctcattgtag                                              20

<210> SEQ ID NO 27
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gcugcuguuc gcugcug                                                 17

<210> SEQ ID NO 28
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gccugcugcu gcugcugcug cugcuggc                                     28

<210> SEQ ID NO 29
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccugucucgc uuuucccuc cgcugcggcc ac                                 32

<210> SEQ ID NO 30
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ggccugccug ccugccugcc ugccugccug ccugcc                            36

<210> SEQ ID NO 31
<211> LENGTH: 45
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 31
gggaagaucu ggccuuccca caagggaagg ccagggaauc uuccc          45

<210> SEQ ID NO 32
<211> LENGTH: 6000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(6000)
<223> OTHER INFORMATION: This sequence may encompass 50-2000 "ctg"
      repeating units wherein some positions may be absent

<400> SEQUENCE: 32
ctgctgctgc tgctgctgct gctgctgctg ctgctgctgc tgctgctgct gctgctgctg     60
ctgctgctgc tgctgctgct gctgctgctg ctgctgctgc tgctgctgct gctgctgctg    120
ctgctgctgc tgctgctgct gctgctgctg ctgctgctgc tgctgctgct gctgctgctg    180
ctgctgctgc tgctgctgct gctgctgctg ctgctgctgc tgctgctgct gctgctgctg    240
ctgctgctgc tgctgctgct gctgctgctg ctgctgctgc tgctgctgct gctgctgctg    300
ctgctgctgc tgctgctgct gctgctgctg ctgctgctgc tgctgctgct gctgctgctg    360
ctgctgctgc tgctgctgct gctgctgctg ctgctgctgc tgctgctgct gctgctgctg    420
ctgctgctgc tgctgctgct gctgctgctg ctgctgctgc tgctgctgct gctgctgctg    480
ctgctgctgc tgctgctgct gctgctgctg ctgctgctgc tgctgctgct gctgctgctg    540
ctgctgctgc tgctgctgct gctgctgctg ctgctgctgc tgctgctgct gctgctgctg    600
ctgctgctgc tgctgctgct gctgctgctg ctgctgctgc tgctgctgct gctgctgctg    660
ctgctgctgc tgctgctgct gctgctgctg ctgctgctgc tgctgctgct gctgctgctg    720
ctgctgctgc tgctgctgct gctgctgctg ctgctgctgc tgctgctgct gctgctgctg    780
ctgctgctgc tgctgctgct gctgctgctg ctgctgctgc tgctgctgct gctgctgctg    840
ctgctgctgc tgctgctgct gctgctgctg ctgctgctgc tgctgctgct gctgctgctg    900
ctgctgctgc tgctgctgct gctgctgctg ctgctgctgc tgctgctgct gctgctgctg    960
ctgctgctgc tgctgctgct gctgctgctg ctgctgctgc tgctgctgct gctgctgctg   1020
ctgctgctgc tgctgctgct gctgctgctg ctgctgctgc tgctgctgct gctgctgctg   1080
ctgctgctgc tgctgctgct gctgctgctg ctgctgctgc tgctgctgct gctgctgctg   1140
ctgctgctgc tgctgctgct gctgctgctg ctgctgctgc tgctgctgct gctgctgctg   1200
ctgctgctgc tgctgctgct gctgctgctg ctgctgctgc tgctgctgct gctgctgctg   1260
ctgctgctgc tgctgctgct gctgctgctg ctgctgctgc tgctgctgct gctgctgctg   1320
ctgctgctgc tgctgctgct gctgctgctg ctgctgctgc tgctgctgct gctgctgctg   1380
ctgctgctgc tgctgctgct gctgctgctg ctgctgctgc tgctgctgct gctgctgctg   1440
ctgctgctgc tgctgctgct gctgctgctg ctgctgctgc tgctgctgct gctgctgctg   1500
ctgctgctgc tgctgctgct gctgctgctg ctgctgctgc tgctgctgct gctgctgctg   1560
ctgctgctgc tgctgctgct gctgctgctg ctgctgctgc tgctgctgct gctgctgctg   1620
ctgctgctgc tgctgctgct gctgctgctg ctgctgctgc tgctgctgct gctgctgctg   1680

| | |
|---|---|
| ctgctgctgc tgctgctgct gctgctgctg ctgctgctgc tgctgctgct gctgctgctg | 1740 |
| ctgctgctgc tgctgctgct gctgctgctg ctgctgctgc tgctgctgct gctgctgctg | 1800 |
| ctgctgctgc tgctgctgct gctgctgctg ctgctgctgc tgctgctgct gctgctgctg | 1860 |
| ctgctgctgc tgctgctgct gctgctgctg ctgctgctgc tgctgctgct gctgctgctg | 1920 |
| ctgctgctgc tgctgctgct gctgctgctg ctgctgctgc tgctgctgct gctgctgctg | 1980 |
| ctgctgctgc tgctgctgct gctgctgctg ctgctgctgc tgctgctgct gctgctgctg | 2040 |
| ctgctgctgc tgctgctgct gctgctgctg ctgctgctgc tgctgctgct gctgctgctg | 2100 |
| ctgctgctgc tgctgctgct gctgctgctg ctgctgctgc tgctgctgct gctgctgctg | 2160 |
| ctgctgctgc tgctgctgct gctgctgctg ctgctgctgc tgctgctgct gctgctgctg | 2220 |
| ctgctgctgc tgctgctgct gctgctgctg ctgctgctgc tgctgctgct gctgctgctg | 2280 |
| ctgctgctgc tgctgctgct gctgctgctg ctgctgctgc tgctgctgct gctgctgctg | 2340 |
| ctgctgctgc tgctgctgct gctgctgctg ctgctgctgc tgctgctgct gctgctgctg | 2400 |
| ctgctgctgc tgctgctgct gctgctgctg ctgctgctgc tgctgctgct gctgctgctg | 2460 |
| ctgctgctgc tgctgctgct gctgctgctg ctgctgctgc tgctgctgct gctgctgctg | 2520 |
| ctgctgctgc tgctgctgct gctgctgctg ctgctgctgc tgctgctgct gctgctgctg | 2580 |
| ctgctgctgc tgctgctgct gctgctgctg ctgctgctgc tgctgctgct gctgctgctg | 2640 |
| ctgctgctgc tgctgctgct gctgctgctg ctgctgctgc tgctgctgct gctgctgctg | 2700 |
| ctgctgctgc tgctgctgct gctgctgctg ctgctgctgc tgctgctgct gctgctgctg | 2760 |
| ctgctgctgc tgctgctgct gctgctgctg ctgctgctgc tgctgctgct gctgctgctg | 2820 |
| ctgctgctgc tgctgctgct gctgctgctg ctgctgctgc tgctgctgct gctgctgctg | 2880 |
| ctgctgctgc tgctgctgct gctgctgctg ctgctgctgc tgctgctgct gctgctgctg | 2940 |
| ctgctgctgc tgctgctgct gctgctgctg ctgctgctgc tgctgctgct gctgctgctg | 3000 |
| ctgctgctgc tgctgctgct gctgctgctg ctgctgctgc tgctgctgct gctgctgctg | 3060 |
| ctgctgctgc tgctgctgct gctgctgctg ctgctgctgc tgctgctgct gctgctgctg | 3120 |
| ctgctgctgc tgctgctgct gctgctgctg ctgctgctgc tgctgctgct gctgctgctg | 3180 |
| ctgctgctgc tgctgctgct gctgctgctg ctgctgctgc tgctgctgct gctgctgctg | 3240 |
| ctgctgctgc tgctgctgct gctgctgctg ctgctgctgc tgctgctgct gctgctgctg | 3300 |
| ctgctgctgc tgctgctgct gctgctgctg ctgctgctgc tgctgctgct gctgctgctg | 3360 |
| ctgctgctgc tgctgctgct gctgctgctg ctgctgctgc tgctgctgct gctgctgctg | 3420 |
| ctgctgctgc tgctgctgct gctgctgctg ctgctgctgc tgctgctgct gctgctgctg | 3480 |
| ctgctgctgc tgctgctgct gctgctgctg ctgctgctgc tgctgctgct gctgctgctg | 3540 |
| ctgctgctgc tgctgctgct gctgctgctg ctgctgctgc tgctgctgct gctgctgctg | 3600 |
| ctgctgctgc tgctgctgct gctgctgctg ctgctgctgc tgctgctgct gctgctgctg | 3660 |
| ctgctgctgc tgctgctgct gctgctgctg ctgctgctgc tgctgctgct gctgctgctg | 3720 |
| ctgctgctgc tgctgctgct gctgctgctg ctgctgctgc tgctgctgct gctgctgctg | 3780 |
| ctgctgctgc tgctgctgct gctgctgctg ctgctgctgc tgctgctgct gctgctgctg | 3840 |
| ctgctgctgc tgctgctgct gctgctgctg ctgctgctgc tgctgctgct gctgctgctg | 3900 |
| ctgctgctgc tgctgctgct gctgctgctg ctgctgctgc tgctgctgct gctgctgctg | 3960 |
| ctgctgctgc tgctgctgct gctgctgctg ctgctgctgc tgctgctgct gctgctgctg | 4020 |

```
ctgctgctgc tgctgctgct gctgctgctg ctgctgctgc tgctgctgct gctgctgctg    4080
ctgctgctgc tgctgctgct gctgctgctg ctgctgctgc tgctgctgct gctgctgctg    4140
ctgctgctgc tgctgctgct gctgctgctg ctgctgctgc tgctgctgct gctgctgctg    4200
ctgctgctgc tgctgctgct gctgctgctg ctgctgctgc tgctgctgct gctgctgctg    4260
ctgctgctgc tgctgctgct gctgctgctg ctgctgctgc tgctgctgct gctgctgctg    4320
ctgctgctgc tgctgctgct gctgctgctg ctgctgctgc tgctgctgct gctgctgctg    4380
ctgctgctgc tgctgctgct gctgctgctg ctgctgctgc tgctgctgct gctgctgctg    4440
ctgctgctgc tgctgctgct gctgctgctg ctgctgctgc tgctgctgct gctgctgctg    4500
ctgctgctgc tgctgctgct gctgctgctg ctgctgctgc tgctgctgct gctgctgctg    4560
ctgctgctgc tgctgctgct gctgctgctg ctgctgctgc tgctgctgct gctgctgctg    4620
ctgctgctgc tgctgctgct gctgctgctg ctgctgctgc tgctgctgct gctgctgctg    4680
ctgctgctgc tgctgctgct gctgctgctg ctgctgctgc tgctgctgct gctgctgctg    4740
ctgctgctgc tgctgctgct gctgctgctg ctgctgctgc tgctgctgct gctgctgctg    4800
ctgctgctgc tgctgctgct gctgctgctg ctgctgctgc tgctgctgct gctgctgctg    4860
ctgctgctgc tgctgctgct gctgctgctg ctgctgctgc tgctgctgct gctgctgctg    4920
ctgctgctgc tgctgctgct gctgctgctg ctgctgctgc tgctgctgct gctgctgctg    4980
ctgctgctgc tgctgctgct gctgctgctg ctgctgctgc tgctgctgct gctgctgctg    5040
ctgctgctgc tgctgctgct gctgctgctg ctgctgctgc tgctgctgct gctgctgctg    5100
ctgctgctgc tgctgctgct gctgctgctg ctgctgctgc tgctgctgct gctgctgctg    5160
ctgctgctgc tgctgctgct gctgctgctg ctgctgctgc tgctgctgct gctgctgctg    5220
ctgctgctgc tgctgctgct gctgctgctg ctgctgctgc tgctgctgct gctgctgctg    5280
ctgctgctgc tgctgctgct gctgctgctg ctgctgctgc tgctgctgct gctgctgctg    5340
ctgctgctgc tgctgctgct gctgctgctg ctgctgctgc tgctgctgct gctgctgctg    5400
ctgctgctgc tgctgctgct gctgctgctg ctgctgctgc tgctgctgct gctgctgctg    5460
ctgctgctgc tgctgctgct gctgctgctg ctgctgctgc tgctgctgct gctgctgctg    5520
ctgctgctgc tgctgctgct gctgctgctg ctgctgctgc tgctgctgct gctgctgctg    5580
ctgctgctgc tgctgctgct gctgctgctg ctgctgctgc tgctgctgct gctgctgctg    5640
ctgctgctgc tgctgctgct gctgctgctg ctgctgctgc tgctgctgct gctgctgctg    5700
ctgctgctgc tgctgctgct gctgctgctg ctgctgctgc tgctgctgct gctgctgctg    5760
ctgctgctgc tgctgctgct gctgctgctg ctgctgctgc tgctgctgct gctgctgctg    5820
ctgctgctgc tgctgctgct gctgctgctg ctgctgctgc tgctgctgct gctgctgctg    5880
ctgctgctgc tgctgctgct gctgctgctg ctgctgctgc tgctgctgct gctgctgctg    5940
ctgctgctgc tgctgctgct gctgctgctg ctgctgctgc tgctgctgct gctgctgctg    6000
```

COMPOUNDS AND METHODS FOR MYOTONIC DYSTROPHY THERAPY

RELATED APPLICATIONS

This application claims priority under 35 U.S.C. §119(e) to U.S. Provisional Patent Application No. 62/034,932, filed Aug. 8, 2014, which is incorporated herein by reference.

SEQUENCE LISTING

The instant application contains a Sequence Listing which has been submitted electronically in ASCII format and is hereby incorporated by reference in its entirety. Said ASCII copy, created on Oct. 23, 2015, is named 500.043US1_SL.txt and is 27,566 bytes in size.

GOVERNMENT SUPPORT

This invention was made with government support under Grant No. R01AR058361 awarded by the National Institutes of Health. The government has certain rights in the invention.

BACKGROUND OF THE INVENTION

Traditionally medicinal chemists have sought to discover and develop therapeutic agents that operate on a single target with high selectivity and affinity. However, it has frequently been found that compounds affecting multiple targets (i.e., "dirty drugs") are superior to those with narrower profiles. Furthermore, advances in "omics" have shown that many diseases are extremely complex. For example, cancer can involve the disregulation of as many as 500 gene products. Thus, a "magic bullet" approach has serious limitations. For these reasons there is currently underway a shift in paradigm from "single drug, single target" to polypharmacologic or, the more rational, multi-target drug discovery (MTDD) approaches. MTDD is not an easy strategy because of the requirement to design drugs that modulate two, three, or multiple disease targets simultaneously. It is very difficult to create fused, hybrid structures where different molecular fragments or segments recognize different targets. A simpler strategy involves tethering together multiple structural domains that each possess different biological activities. These ligands may be the conjugate of two known inhibitors, such as two proteins in a particular signaling pathway, or they may be a binding unit and a reactive moiety covalent linked. Either way, effective examples of this kind of therapy are still needed if this approach is to make it to the clinic.

Myotonic dystrophy type 1 (DM1) is an autosomal dominant neuromuscular disorder characterized by a range of symptoms that include muscle weakness (myopathy), difficulty relaxing muscles (myotonia), progressive muscle wasting (atrophy), cataracts, cardiac defect, and insulin dependent diabetes. There is an urgent need to discover lead agents for treating DM1 because it affects about 1 in 8,000 people, yet it remains incurable with no direct therapeutic options.

DM1 results from a progressive expansion of the trinucleotide CTG repeat in the 3'-untranslated region of the dystrophia myotonia protein kinase (DMPK) gene on chromosome 19q13.3. The number of CTG repeats is less than 35 in healthy people, and ranges from 50 to thousands in DM1 patients. The molecular origin of DM1 was previously attributed to three possible mechanisms: (1) DMPK haploinsufficiency, (2) decreased expression of neighboring genes, including SIX5 and DMAHP, and (3) a gain-of-function for the expanded RNA transcript ($rCUG^{exp}$). Recent studies have argued against the first two hypotheses, leaving the third mechanism as the favored one for therapeutic intervention.

The gain of function model involves expanded rCUG repeats forming stable stem-loop structures with U-U mismatches flanked by G-C and C-G base pairs, and sequestering important proteins. Key among these proteins is the muscleblind-like (MBNL) protein, a key alternative splicing regulator. The loss of MBNL1 results in the abnormal alternative splicing of more than 100 pre-mRNAs, including the cardiac troponin T (cTNT), insulin receptor (IR) and chloride channel 1 (ClC-1). Supporting the toxic RNA model is the finding that overexpression of MBNL1 protein in the skeletal muscle of a DM1 mouse model relieved the myotonia and abnormal RNA splicing. The MBNL1-$rCUG^{exp}$ complex formation has emerged as a key therapeutic target for DM1. Because there are currently no effective therapies for DM1, there is an urgent need for a new compounds and methods for the study and treatment of the disease.

SUMMARY

The invention provides acridine- and bisamidinium-based inhibitors that can be used as therapeutic agents, for example, for the treatment of myotonic dystrophy type 1 (DM1). The invention also provides potent inhibitors of protein sequestration by expanded triplet (CUG) repeats. Administration of the inhibitors can provide phenotype reversal, which has been demonstrated in a *Drosophila* model of DM1.

The invention thus provides a compound of Formula I:

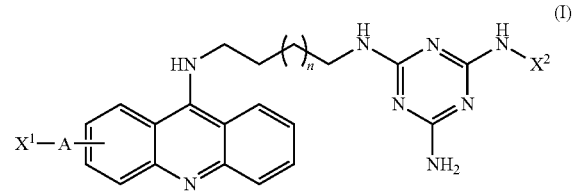

wherein
n is 0, 1, or 2;
A is a direct bond or —C(=O)NH—;
$X^1$ and $X^2$ are each independently —H, —C(=O)NHCH$_2$CH$_2$N(CH$_2$CH$_2$NH$_2$)$_2$, or a moiety of Formula C1:

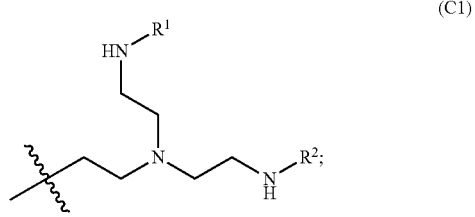

wherein $R^1$ and $R^2$ are each independently —H or a moiety of Formula C2:

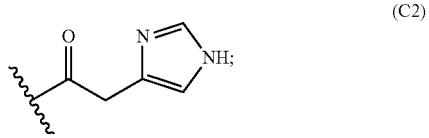 [SMILES: *C(=O)Cc1c[nH]cn1]

wherein at least one of $X^1$ and $X^2$ is not —H; or a salt or solvate thereof.

In one embodiment, $X^1$ is H. In another embodiment, $X^1$ is —C(=O)NHCH$_2$CH$_2$—N(CH$_2$CH$_2$NH$_2$)$_2$. In yet another embodiment, $X^1$ is a moiety of Formula C1. When $X^1$ is a moiety of Formula C1, one embodiment provides a compound wherein $R^1$ of the moiety of Formula C1 is H. In another embodiment, $R^1$ of the moiety of Formula C1 is a moiety of Formula C2. In certain specific embodiments, $R^1$ and $R^2$ are each H. In other embodiments, $R^1$ and $R^2$ are both a moiety of Formula C2. In yet another embodiment, $R^1$ of the moiety of Formula C1 is H and $R^2$ is a moiety of Formula C2.

In one embodiment, $X^2$ is H. In another embodiment, $X^2$ is —C(=O)NHCH$_2$CH$_2$—N(CH$_2$CH$_2$NH$_2$)$_2$. In yet another embodiment, $X^2$ is a moiety of Formula C1. When $X^2$ is a moiety of Formula C1, one embodiment provides a compound wherein $R^1$ of the moiety of Formula C1 is H. In another embodiment, $R^1$ of the moiety of Formula C1 is a moiety of Formula C2. In certain specific embodiments, $R^1$ and $R^2$ are both H. In other embodiments, $R^1$ and $R^2$ are both a moiety of Formula C2. In yet another embodiment, $R^1$ of the moiety of Formula C1 is H and $R^2$ is a moiety of Formula C2.

The invention also provides a compound of Formula II:

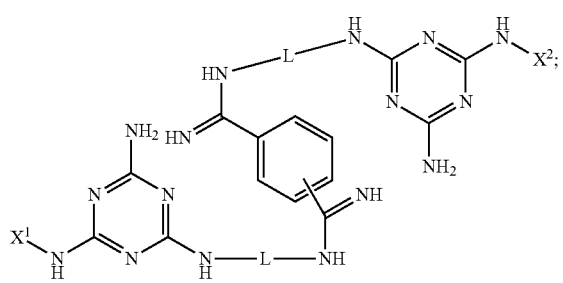

(II)

wherein
each L is independently —(C$_3$-C$_5$)alkylene-, —(C$_2$-C$_5$)alkylene- interrupted by one oxygen, 1,3-cyclopenylene, 1,3-cyclohexylene, or 1,4-cyclohexylene;
$X^1$ and $X^2$ are each independently —H, —C(=O)NHCH$_2$CH$_2$N(CH$_2$CH$_2$NH$_2$)$_2$, or a moiety of Formula C1:

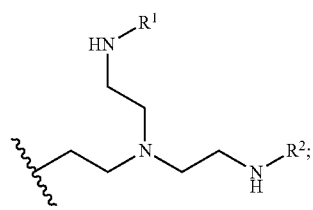

(C1)

wherein $R^1$ and $R^2$ are each independently —H or a moiety of Formula C2:

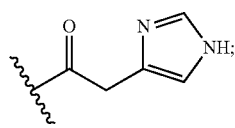

(C2)

wherein at least one of $X^1$ and $X^2$ is not —H;
or a salt or solvate thereof.

In one embodiment, $X^1$ is H. In another embodiment, $X^1$ is —C(=O)NHCH$_2$CH$_2$—N(CH$_2$CH$_2$NH$_2$)$_2$. In yet another embodiment, $X^1$ is a moiety of Formula C1. When $X^1$ is a moiety of Formula C1, one embodiment provides a compound wherein $R^1$ of the moiety of Formula C1 is H. In another embodiment, $R^1$ of the moiety of Formula C1 is a moiety of Formula C2. In certain specific embodiments, $R^1$ and $R^2$ are both H. In other embodiments, $R^1$ and $R^2$ are both a moiety of Formula C2. In yet another embodiment, $R^1$ of the moiety of Formula C1 is H and $R^2$ is a moiety of Formula C2.

In one embodiment, $X^2$ is H. In another embodiment, $X^2$ is —C(=O)NHCH$_2$CH$_2$—N(CH$_2$CH$_2$NH$_2$)$_2$. In yet another embodiment, $X^2$ is a moiety of Formula C1. When $X^2$ is a moiety of Formula C1, one embodiment provides a compound wherein $R^1$ of the moiety of Formula C1 is H. In another embodiment, $R^1$ of the moiety of Formula C1 is a moiety of Formula C2. In certain specific embodiments, $R^1$ and $R^2$ are both H. In other embodiments, $R^1$ and $R^2$ are both a moiety of Formula C2. In yet another embodiment, $R^1$ of the moiety of Formula C1 is H and $R^2$ is a moiety of Formula C2.

In any embodiment described herein, the substituents on the central phenyl ring of Formula II can be in an ortho, meta, or para orientation with respect to each other. In certain specific embodiments, the substituents on the central phenyl ring of Formula I are in a para orientation. In other embodiments, the substituents on the central phenyl ring of Formula II are in meta or ortho orientations. Accordingly, the compound of Formula II can be a compound of Formula IIA:

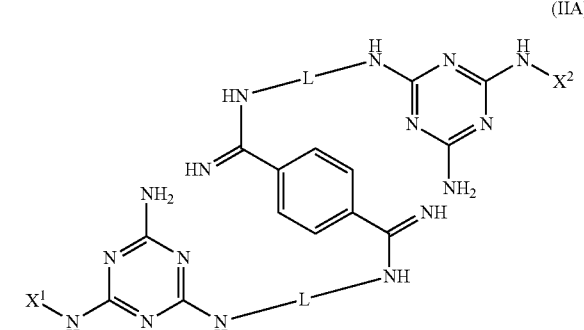

(IIA)

wherein each variable is as defined for Formula II.

The variables L can be characterized as linker groups. In any embodiment described herein, the variables L can be the same or different from each other. When L is a —(C$_2$-C$_5$)alkylene- interrupted by one oxygen, the resulting linker L can thus be —CH$_2$OCH$_2$—, —CH$_2$OCH$_2$CH$_2$—, —CH$_2$CH$_2$OCH$_2$—, —CH$_2$OCH$_2$CH$_2$CH$_2$—, —CH$_2$CH$_2$CH$_2$OCH$_2$—, —CH$_2$CH$_2$OCH$_2$CH$_2$—, —CH$_2$OCH$_2$CH$_2$CH$_2$CH$_2$—, —CH$_2$CH$_2$OCH$_2$CH$_2$CH$_2$—, and the like. Several embodiments include compounds where each L, independently of one another, is propylene, butylene, or pentylene. Accordingly, a compound of Formula II or IIA can be a compound of Formula III:

(III)

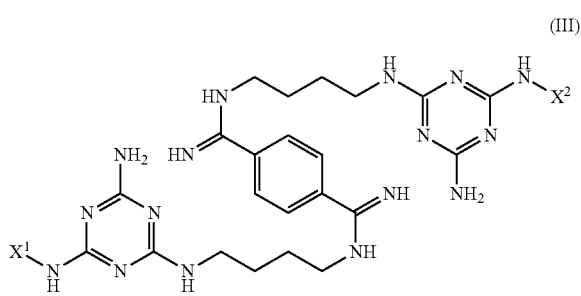

wherein $X^1$ and $X^2$ are as defined for Formula II; or a salt or solvate thereof Specific compounds of Formulas I, II, IIA, and III include:

(4)

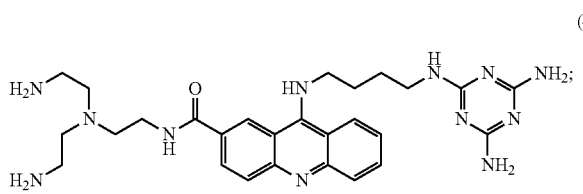

(5)

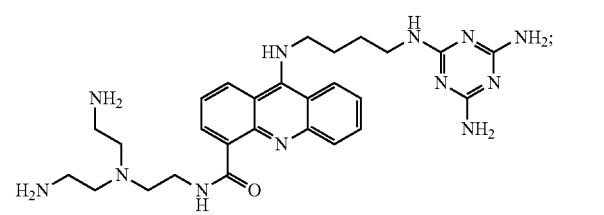

(6)

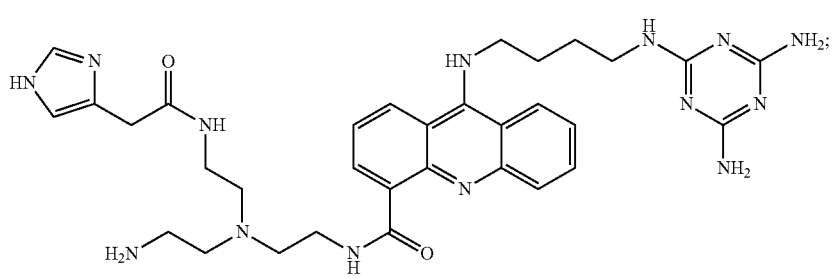

(6-1)

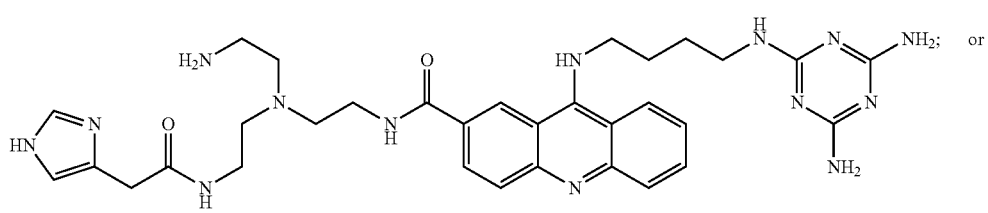

(9)

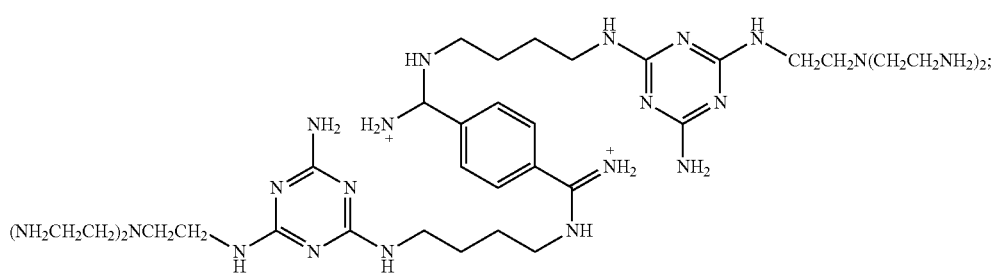

or a salt or solvate thereof; or a combination thereof, optionally in a pharmaceutical composition.

In an additional embodiment, the invention provides a method of reducing the symptoms of myotonic dystrophy comprising administering to a patient having myotonic dystrophy an effective amount of a compound of Formula I or II, thereby reducing the symptoms of the myotonic dystrophy.

Compounds of Formula I and II are typically prepared and/or isolated as salts, such as their di, tri, tetra, octa, or nona HCl salts. However, the compounds can be prepared and isolated as a variety of other salts or solvates, such as a salt described herein below, and as would be readily recognized by one of skill in the art.

The invention further provides a pharmaceutical composition comprising one or more compounds of Formula I or Formula II, or a sub-Formula thereof, in combination with a pharmaceutically acceptable diluent, carrier, or excipient.

The invention further provides a method of reducing the symptoms of myotonic dystrophy. The method can include administering to a patient having myotonic dystrophy an effective amount of a compound of Formula I or Formula II, thereby reducing the symptoms of the myotonic dystrophy. The myotonic dystrophy can be myotonic dystrophy type 1 (DM1). The symptoms reduced by the administration can be, for example, one or more of muscle weakness (myopathy), difficulty relaxing muscles (myotonia), progressive muscle wasting (atrophy), cataracts, cardiac defects, and insulin dependent diabetes.

The invention thus provides novel compounds and compounds of the formulas described herein, intermediates for the synthesis of compounds and compounds of the formulas described herein, as well as methods of preparing the compounds. The invention also provides compounds that are useful as intermediates for the synthesis of other useful compounds. The invention further provides for the use of compounds and compounds of the formulas described herein for the manufacture of medicaments useful for the treatment of diseases in a mammal, such as a human. Thus, the invention provides for the use of the compounds and compositions described herein for use in medical therapy, such as the treatment of myotonic dystrophy. The compositions can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a specific example, or a certain aspect of the invention. However, one skilled in the art will understand that portions of the example or aspect may be used in combination with other examples or aspects of the invention.

FIG. 4A-B. Time- and dose-dependent cleavage experiments of ligand 9 using (CUG)$_{16}$ (SEQ ID NO: 1). (a) EtBr post-staining gels. (b) Quantitative analysis of changes in (CUG)$_{16}$ (SEQ ID NO: 1) intensity. The mixture was loaded on 20% denaturing PAGE gels. The percentage of (CUG)$_{16}$ (SEQ ID NO: 1) intensity was normalized to the control (no compound). Left column, 5 h; right column, 48 h. Error bars represent standard errors of mean of three independent experiments.

FIG. 5A-C. Selectivity study. (a) Structures of RNA oligonucleotides (SEQ ID NOS 27-31, respectively, in order of appearance) tested in selectivity study. "(CUG)$_4$" is disclosed as SEQ ID NO: 10, "(CUG)$_{16}$" is disclosed as SEQ ID NO: 1, and "(CCUG)$_8$" is disclosed as SEQ ID NO: 11. Cleavage gels of ligands 6 (b; "(CCUG)$_8$" is disclosed as SEQ ID NO: 11) and 9 (c; "(CUG)$_{16}$" is disclosed as SEQ ID NO: 1, "(CUG)$_4$" is disclosed as SEQ ID NO: 10, and "(CCUG)$_8$" is disclosed as SEQ ID NO: 11). RNA (100 nM) was incubated with ligands for 19 h at 37° C. The reaction mixture was loaded on a 20% denaturing PAGE gel, followed by post-staining with EtBr.

FIG. 7A-B. CUG$^{exp}$ mRNA levels in DM1 model cells. (a) Effects of 5, 6 and 9 on CUG$^{exp}$ mRNA levels at 3 d 50 μM treatment ("(CUG)$_{960}$" is disclosed as SEQ ID NO: 7). (b) Ligand 9 reduced CUG$^{exp}$ mRNA levels in a dose dependent fashion ("(CUG)$_{960}$" is disclosed as SEQ ID NO: 7). Error bars represent the standard error of mean of at least three independent experiments. * P<0.01; ** P<0.005 (two tailed t-test).

FIG. 8A-B. In vitro transcription of (CTG.CAG)$_{74}$ (SEQ ID NOS 3-4, respectively). Ligands at different concentrations were incubated with 15 ng linearized plasmids in T7 RNA polymerse mixture at 37° C. After 2 h, the reaction mixture was on a 8% denaturing gel. (a) Transcription gels of ligands at different concentrations ("(CUG)$_{74}$" is disclosed as SEQ ID NO: 22). (b) Plot of the percentage of transcription inhibition versus ligand concentrations. The error bars represent standard errors of mean of three independent experiments. Untreated at 100 μM is at 0%; ligand 2 at 100 μM is at ~10%; ligand 7 at 100 μM is at ~35%; ligand 6 at 100 μM is at ~80%; ligand 9 at 100 μM is at ~96%; and ligand 5 at 100 μM is at ~99%.

FIG. 9A-D. Biological activities of ligands in DM1 Drosophila. (a) Ligands 2 and 9 improved the neurodegeneration in DM1 Drosophila at 6 days age; 9 showed better effects than 2 under the same conditions. (b) Larvae improved the mobility ability under the treatment of ligands. The error bars represent standard deviation of three independent experiments. For each independent experiment, 10 individual larvae were studied. (c) Diagram of i(CTG)$_{60/480}$ (SEQ ID NOS 5-6, respectively) gene construct and the region (SV40 terminator) that was amplified to measure the level of transcribed mRNA. (d) Ligand 9 reduced the levels of SV40 RNA in larvae. The SV40 region of the CUG-containing RNA was measured relative to fl-actin RNA level. The error bars represent the standard deviation of three independent experiments. For each independent experiment, mRNA levels from 5 individual larvae were determined; * P<0.05,  P<0.01, * P<0.001 (two tailed t-test). "(CTG)$_{60/480}$" is disclosed as SEQ ID NOS 5-6, respectively, in FIGS. 9A-D.

FIG. 10A-B. Cleavage gel of ligands with TAMRA-(CUG)$_{16}$ (SEQ ID NO: 1). (a) The full cleaving gel of ligand 9 and control C. Ligand 9 or a control C as a mixture of 2 (100 μM) and 10 (100 μM) were incubated with T-(CUG)$_{16}$ (SEQ ID NO: 1) (100 nM) in a Tris buffer (50 mM, pH 7.4) supplemented with 150 mM NaCl and 2 mM MgCl$_2$. "OH" is a control in which RNA was incubated in a buffer with pH of 10.6. The reaction mixture was run on a 20% denaturing PAGE gel. (b) Cleaving gel of ligands 6, 9, and controls after 20 h incubation. OH: RNA was incubated with 1% KOH, C1: RNA was incubated with a mixture of ligands 7 (100 μM) and 10 (100 μM); C2: RNA was incubated with a mixture of ligands 2 (100 μM) and 10 (100 μM). The reaction was stopped by adding 8 μL of urea (8 M) and 2 μL of RNA loading dye to 10 μL of the reaction mixture and the sample was loaded on a 20% denaturing PAGE gel.

FIG. 11A-B. Ligand 9 rescued splicing defect of IR minigene. (a) Mis-splicing of IR minigene in DM1 model cells. (b) Percentage of exon 11 inclusion in HeLa (healthy model cell). DT960 (HeLa co-transfected with IR plasmid and DT960 plasmid expressing $(CUG)_{960}$ (SEQ ID NO: 7)), and DT960 cells treated with 9. The splicing experiments were performed following the reported protocol (Wong et al., *J. Am. Chem. Soc.* 136, 6355-6361 (2014)). Error bars represent the standard error of mean from at least three independent experiments. * P<0.05, ** P<0.005 (two tailed t-test).

FIG. 12. $CUG^{exp}$ mRNA level after treatment with ligand 5. Error bars represent standard deviations from three independent experiments, the data point for 7 d treatment was from two independent experiments. * P<0.05, *** P<0.001 (two tailed t-test).

FIG. 13A-B. In vitro transcription gels. (a) Control ligand 10 showed a negligible effect on in vitro transcription of $(CTG.CAG)_{74}$ (SEQ ID NOS 3-4, respectively) ("$(CUG)_{74}$" is disclosed as SEQ ID NO: 22). (b) Effects of ligands 6 and 9 on the transcription of control plasmids that contain no CTG.CAG repeats. Ligand 6 showed a negligible transcription inhibition whereas 9 strongly inhibited the formation of control plasmids at 100 and 50 μM.

FIG. 14. In vitro transcription of $(CTG.CAG)_{74}$ (SEQ ID NOS 3-4, respectively) in presence of $(CUG)_{16}$ (SEQ ID NO: 1). Plot of % transcription inhibition versus different concentrations of the ligand. The error bars represent the standard error of the mean from three independent experiments.

FIG. 15A-C. Rescuing disease phenotypes in DM1 *Drosophila* with ligands 2 and 9. (a) Treatment of *Drosophila* bearing $i(CUG)_{60}$ (SEQ ID NO: 8) with ligands 2 and 9 showed no effects on larval locomotion (left) and eyes (right), indicating that the ligands are relatively non-toxic. The error bars represent the standard deviation of three independent experiments ("$(CTG)_{60}$" is disclosed as SEQ ID NO: 5). (b) Ligands 2 and 9 reversed the disease phenotype in DM1 inflicted fly eyes at the concentration of 200 μM ("$(CTG)_{480}$" is disclosed as SEQ ID NO: 6). (c) Ligand 9 rescued DM1 phenotypes in larval eyes in a dose-dependent manner ("$(CTG)_{480}$" is disclosed as SEQ ID NO: 6).

DETAILED DESCRIPTION

Figure 1:
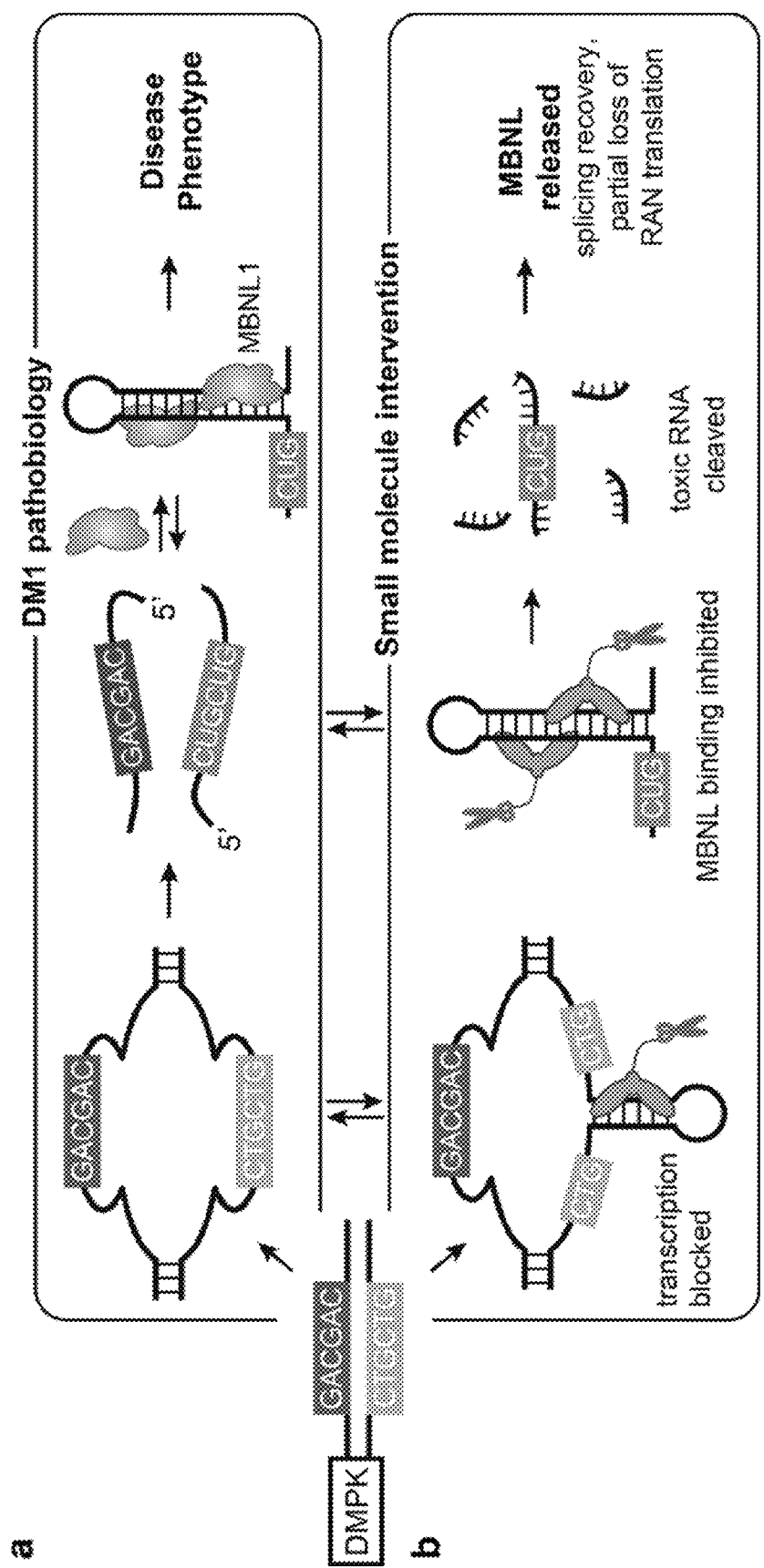
FIG. 1A-B. Schematic illustration of DM1 pathobiology and multi-target treatment. (a) RNA gain-of-function disease pathogenesis. The expanded DNA trinucleotide repeat (CTG$^{exp}$) undergoes transcription to form CUG$^{exp}$ hairpin that sequesters MBNL protein (e.g., MBNL1). The MBNL level depletion causes splicing defects of more than 100 pre-mRNAs, resulting in disease symptoms. RAN translation of CUG$^{exp}$ and CAG$^{exp}$ generates toxic homopeptides. (b) Small molecule intervention. Small molecules (schematically illustrated as binding to the nucleic acids) target CTG$^{exp}$ hairpin inhibiting production of CUG$^{exp}$. Any CUG$^{exp}$ formed is bound by the small molecules, inhibiting MBNL and other protein sequestration. Cleaving functionality (schematically illustrated as scissors) processes the toxic RNA eliminating it. All the small molecule interventions free MBNL for its normal functions. Likewise, other toxic pathways induced by the CUG$^{exp}$ are eliminated.

Single-agent, single-target therapeutic approaches are often limited by a complex disease pathobiology. Herein we report rationally designed multi-targeting therapeutic agents for myotonic dystrophy type 1 (DM1), an incurable neuromuscular disease that originates in an abnormal expansion of CTG repeats ($CTG^{exp}$) in the DMPK gene. Several rationally designed small molecules were found to target the DM1 pathobiology in vitro in three distinct ways: (1) binding the expanded trinucleotide repeat, $CTG^{exp}$, and inhibiting its transcription to the toxic $CUG^{exp}$ RNA, (2) binding the $CUG^{exp}$ RNA and releasing sequestered muscleblind-like protein (MBNL1), and (3) cleaving the toxic $CUG^{exp}$ in an RNase-like manner. Importantly, the compounds can reduce the levels of $CUG^{exp}$ in DM1 model cells and reverse two separate $CUG^{exp}$-induced phenotypes in a DM1 *Drosophila* model, thus demonstrating their therapeutic efficacy.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups (groups from which a proton can be removed (e.g., —COOH) or added (e.g., amines) or which can be quaternized (e.g., amines)). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can be a monovalent hydrocarbon radical, as described and exemplified above, or it can be a divalent hydrocarbon radical (i.e., an alkylene).

The alkyl groups of the various R groups, as well as the amino substituents of triazine rings and the central phenyl ring of the formulas described herein may be substituted with one or more substituents. The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group. The substituents described above and throughout this specification can be applied to any synthetically available position of the various compounds described herein, including amine groups on the compounds described in U.S. Pat. No. 8,754,084 (Zimmerman et al.), which includes useful synthetic techniques and which is incorporated herein by reference. The linkers described in U.S. Pat. No. 8,754,084 (Zimmerman et al.) may also be used as the group L in Formula I and related formulas described herein.

The term "amino" refers to —NH$_2$, and the term "alkylamino" refers to —NR$_2$, wherein at least one R is alkyl and the second R is hydrogen, alkyl, a nitrogen protecting group or an optionally substituted substituent as described herein. The term "acylamino" refers to RC(=O)NH—, wherein R is as described previously.

The term "exposing" is intended to encompass the term as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a therapeutic agent.

The term "contacting" refers to the act of touching, making contact, or of bringing to immediate or close proximity (i.e., exposing), including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. A "therapeutically effective amount" of a compound with respect to the subject method of treatment refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated, e.g., at a reasonable benefit/risk ratio applicable to any medical treatment.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. The term "treating" or "treatment" thus can include reversing, reducing, or arresting the symptoms, clinical signs, and underlying pathology of a condition in manner to improve or stabilize a subject's condition. However, when preventing is intended, it will be explicitly stated.

The terms "inhibit", "inhibiting", and "inhibition" refer to the slowing, halting, or reversing the growth or progression of a disease, infection, condition, or activity of a group of cells or an enzyme. The inhibition can be greater than about 20%, 40%, 60%, 80%, 90%, 95%, or 99%, for example, compared to the growth or progression that occurs in the absence of the treatment or contacting.

The phrase "maximum tolerated dose" is employed herein to refer to the highest dose of a pharmacological treatment that will produce the desired effect without unacceptable toxicity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Embodiments of the Invention

Although multi-target drug discovery (MTDD) efforts have largely focused on protein targets, the increasing importance of RNA as a therapeutic target makes it an excellent candidate for MTDD. We were particularly attracted to myotonic dystrophy type 1 (DM1) because its complicated disease pathogenesis is increasingly well-understood, providing well-defined DNA, RNA, and protein targets for a small molecule MTDD approach. DM1 is an incurable, multi-systemic neuromuscular disease that is caused by an abnormal expansion of the CTG trinucleotide repeats (CTG$^{exp}$) in the 3'-untranslated region of the DMPK gene on chromosome 19q13 (see FIG. 1a (top scheme)). This expanded DNA, which can reach 50-2000 CTG repeats (SEQ ID NO: 32), yields an expanded CUG RNA transcript (CUG$^{exp}$) that sequesters the alternative-splicing regulator muscle blind-like protein (MBNL), leading to splicing defects and disease symptoms.

We previously developed small molecules that inhibit the MBNL1 sequestration by $CUG^{exp}$. However, a recently expanded view of DM1 pathogenesis has suggested that additional $CUG^{exp}$-induced toxic pathways must be considered for the disease phenotype to be fully reversed. In particular, the CTG.CAG repeats undergo bi-directional transcription producing two transcripts, $CUG^{exp}$ and $CAG^{exp}$, that both undergo repeat-associated non-ATG (RAN) translation, generating multiple toxic homopeptides. Further, it has been shown that $CUG^{exp}$ disrupts the translation of the MEF2 protein, which affects multiple levels of mRNA and microRNA in human DM1 heart tissues. Furthermore, the discoveries of other proteins involved in the formation of MBNL1-$CUG^{exp}$ foci suggest that other toxic pathways may be induced by $CUG^{exp}$.

The studies discussed above suggest that a multi-target drug approach, especially one that degrades toxic $CUG^{exp}$ or inhibits its formation may be more effective. We report herein a rational MTDD effort leading to small molecules that intervene in three separate steps in the DM1 pathobiology, suppressing $CUG^{exp}$ mRNA levels and reversing the disease phenotype in DM1 model cells and a DM1 *Drosophila* model.

Multi-Target Ligand Design.

Our overall approach was to develop agents able to intervene in the DM1 mechanism in three ways: (1) targeting $CTG^{exp}$ to inhibit its transcription to $CUG^{exp}$, (2) target $CUG^{exp}$ to inhibit MBNL1 sequestration, and (3) hydrolytically degrading the $CUG^{exp}$ with RNase-like catalytic functionality (see FIG. 1*b* (bottom scheme)). We previously reported two classes of rationally-designed agents (e.g., 1 and 2) that selectively bound $CUG^{exp}$ and inhibited MBNL binding with low micromolar $K_I$ values.

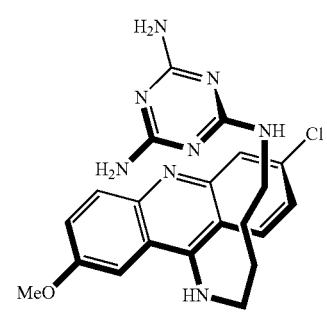

(1)

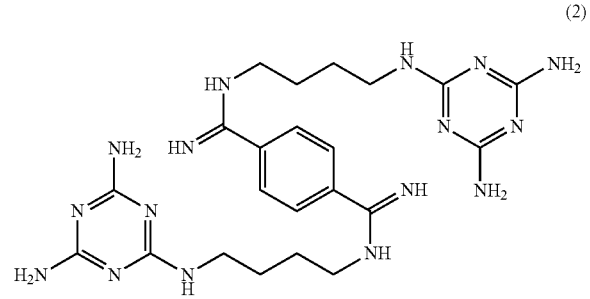

(2)

Both ligands feature triaminotriazine moieties to recognize the UU mismatch in duplex $CUG^{exp}$ and provide sequence selectivity, whereas the acridine group in 1 and the bisamidinium unit in 2 were selected to drive the association by A-form RNA intercalation and groove binding, respectively.

Although 1 was not cell permeable, analog 3 utilized the polyamine transport system to enter cells.

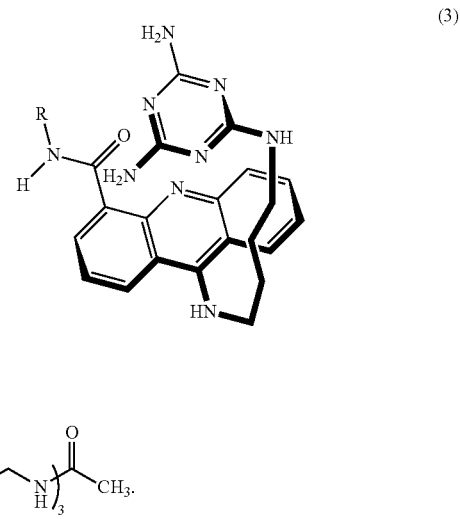

(3)

The bisamidinium unit in 2 was chosen partly because it was reported to localize in cell nuclei. Indeed, both 2 and 3 dissolved the MBNL1-$CUG^{exp}$ nuclear foci and partially rescued splicing defects of IR and cTNT minigenes in DM1 model cell cultures.

In comparison to 1, bisamidinium-containing 2 showed similar in vitro inhibition potency, but with lower toxicity, higher water solubility, and better cell uptake. Nonetheless, the acridine ligands are inherently multi-targeting because of their ability to bind both the DNA and RNA causing DM1. Thus, agent 1 complexes an oligonucleotide 10-mer containing a single dCTG and rCUG site with $K_D$=0.39±0.08 nM and $K_D$=0.43±0.11 nM, respectively. In contrast, agent 2 is selective for $CUG^{exp}$, showing no detectable binding of dCTG by ITC (vide infra). Because of the dual binding ability of 1, we investigated its potential as a transcription inhibitor. Thus, DM1 model cells were treated with 3, the cell permeable analog of 1, as well as with 2 as a control. The $CUG^{exp}$ mRNA levels were determined using a known protocol (vide infra) (Lee et al., *Proc. Natl. Acad. Sci. U.S.A.* 109, 4221-4226 (2012)). Because neither 1 nor 3 exhibited any ability to modulate the $CUG^{exp}$ mRNA levels, attention was turned to the targeted degradation of the toxic $CUG^{exp}$ RNA.

Numerous small molecule mimics of RNase A were developed over the past few decades. Many use the active-site functional groups found in RNase A in an effort to mimic its well-established acid-base mechanism of action. Although none of the mimics cleaved RNA as effectively as RNase A, those containing at least one ammonium ion and an imidazole or amino group were the most promising. Based on this information, we designed agents 4-6, 8, and 9 with sidechains at the 2- or 4-position of the acridine ring (4-6) or attached to the triaminotriazine rings (8 and 9), each of which are illustrated below.

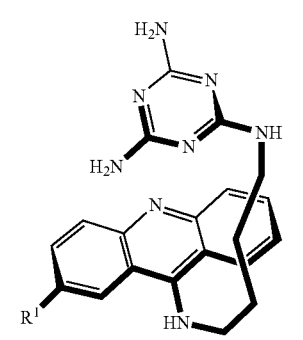

R[1] = CONHCH$_2$CH$_2$N(CH$_2$CH$_2$NH$_2$)$_2$;   (4)

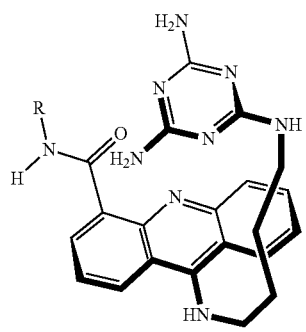

R = CH$_2$CH$_2$N(CH$_2$CH$_2$NH$_2$)$_2$   (5)

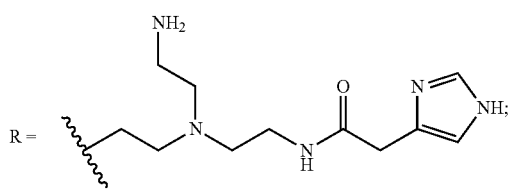

(6)

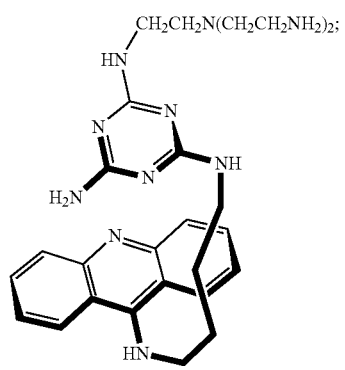

(8)

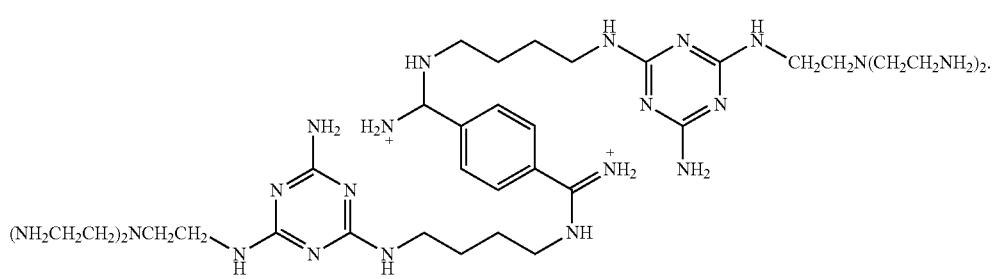

(9)

The ability of these potentially catalytic functional groups to function in the desired fashion was established by modeling. The ligands were docked to binding sites prepared from the published X-ray analysis of (CUG)$_6$ (SEQ ID NO: 9) (PDB: 3GM7) using MOE and each was found to reach at least one putative scissile phosphate bond. The synthesis of cleaving agents 4-6, 8, and 9 is described herein below and generally involves conjugation of di-Boc-protected tris(2-aminoethyl) amine with the appropriate acridine acid chloride or chlorotriazine. The imidazole-bearing agent 6 was prepared from 5 by coupling one amino group with imidazole-4-acetic acid. The additional functional groups improved the water solubility, cell penetration, and affinity toward CUG$^{exp}$.

In Vitro CUG$^{exp}$ Cleavage by Small Molecules 4-9.

Figure 2:
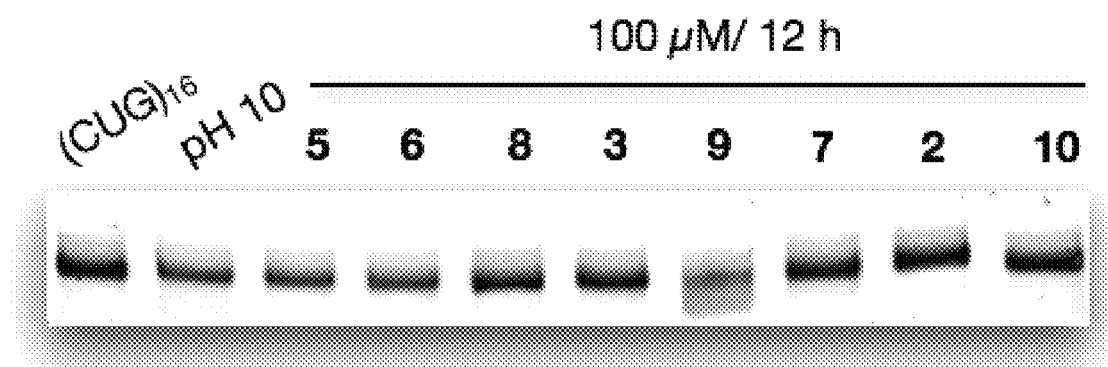
FIG. 2. Cleavage screening gel. (CUG)$_{16}$ (SEQ ID NO: 1) (100 nM) was incubated with ligands (100 μM) and (CUG)$_{16}$ (SEQ ID NO: 1) (100 nM), 12 h, 37° C. The reaction mixture was loaded onto a 20% denaturing PAGE gel and RNA was detected by post-staining with EtBr.

The potential cleavage activity of 4-9 was screened using a simple gel shift assay with (CUG)$_{16}$ (SEQ ID NO: 1). To screen the agents, each agent was incubated for 12 h with unlabeled (CUG)$_{16}$ (SEQ ID NO: 1) at a final concentration of 100 µM at pH 7.4. The mixture was separated on an RNA denaturing gel and stained with EtBr (FIG. 2). No loss of (CUG)$_{16}$ (SEQ ID NO: 1) intensity was observed upon treatment with 2, 7, or tris(2-aminoethyl)amine (10).

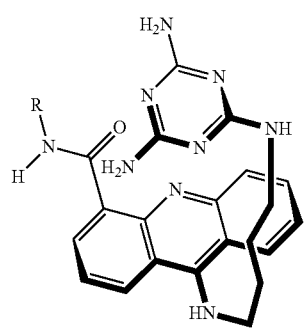

R = CH$_3$;   (7)

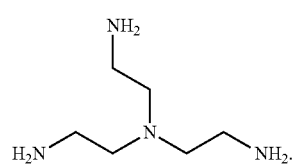

(10)

These three control experiments demonstrate that a polyamine or the CUG-targeting acridine- or bisamidinium-ligand on its own is insufficient to alter the $(CUG)_{16}$ (SEQ ID NO: 1). In contrast a decrease in $(CUG)_{16}$ (SEQ ID NO: 1) intensity was observed for all ligands containing amino groups (i.e., 4-6, 8, and 9), demonstrating RNA cleavage (FIG. 2). At least qualitatively, agents 6 and 9 appeared to be most active.

Figure 3:
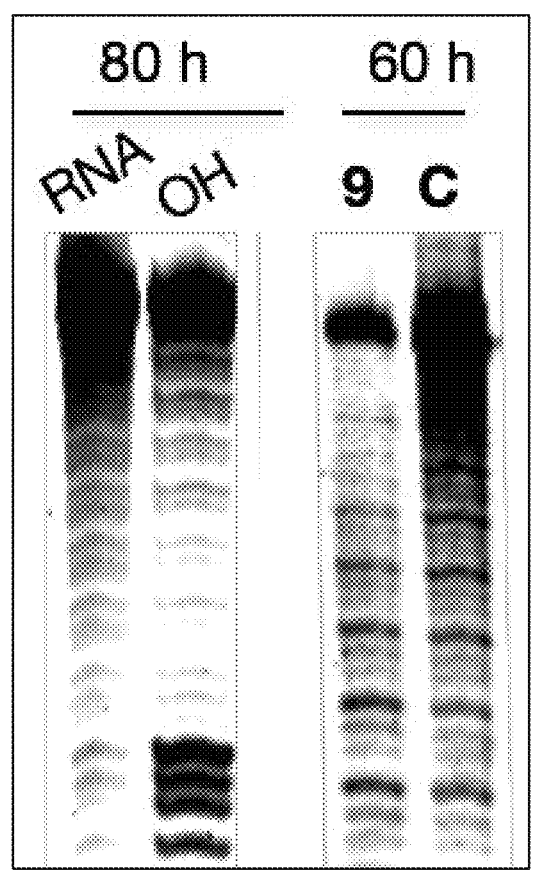
FIG. 3. Partial TAMRA-(CUG)$_{16}$ (SEQ ID NO: 1) cleavage gel. Ligand 9 or a control C as mixture of 2 (100 μM) and 10 (100 μM) were incubated with T-(CUG)$_{16}$ (SEQ ID NO: 1) (100 nM) in a Tris buffer (50 mM, pH 7.4) supplemented with 150 mM NaCl and 2 mM MgCl$_2$. "OH" is a control with RNA incubated in a buffer with pH 10.6. The reaction mixture was run on a 20% denaturing PAGE gel. See FIG. 10 for full gel.

To observe potential cleavage fragments that were not observable in the screening gel due to the relative insensitivity of the EtBr post-staining, we performed similar experiments using TAMRA labeled $(CUG)_{16}$ (SEQ ID NO: 1) (T-$(CUG)_{16}$ (SEQ ID NO: 1)). As seen in FIG. 3, after 60 h of incubation, agent 9 shows a large number of bands. Interestingly, the intensity pattern corresponds to the repeat sequence, with every fourth band significantly more intense. This pattern may indicate a specific positioning of the catalytic groups by the ligand or possibly a higher reactivity of the UU mismatch site. Similarly, less distinct results were seen at shorter (20 h) incubation times (see FIG. 10, which includes data for 6 and 9). Some RNA fragments were observed for a control incubation using a combination of ligand 2 and tetraamine 10, but the reaction is much slower (FIG. 3, gel labeled C). Given the simplicity and ease of quantifying the loss of unlabeled $(CUG)_{16}$ (SEQ ID NO: 1) in the screening assay above, agent 9 was reexamined at four different concentrations (5-100 µM) and three times. As seen in FIG. 4, loss of the $(CUG)_{16}$ (SEQ ID NO: 1) band was both time- and dose-dependent.

To better determine the origin of the loss of $CUG^{exp}$ mRNA, the reaction of $(CUG)_4$ (SEQ ID NO: 10) with a 3'-TEG-biotin tag and 6 was monitored by MALDI. After 5 h of incubation with 6, fragment peaks were observed with lower m/z values, but no major change was seen in control samples. The m/z values found matched the calculated m/z corresponding to hydrolysis products with 3'-hydroxyl end-groups and selective cleavage in the loop and immediately adjacent to the loop. Cleavage experiments at different pH values and different concentrations of $Mg^{2+}$ were carried out. The data from these experiments showed that the cleavage activity of ligand 9 was $Mg^{2+}$-independent and increased with pH (e.g., pH 6-11). The higher pH increases the concentration of the expected active species containing one amino group and one ammonium ion. However, higher pH also increases the background hydroxide-catalyzed reaction.

Selectivity of $CUG^{exp}$ Cleaving Agents.

Off target activity is a concern for any therapeutic agent but especially one designed to cleave RNA. To test the selectivity of agents 6 and 9, the screening gel assay described above was applied to other RNA targets, specifically cTNT32, $(CCUG)_8$ (SEQ ID NO: 11), and HIV-1 frameshift site RNA (HIV FS) (FIG. 5a). Both 6 and 9 were quite selective. Thus, neither agent showed detectable cleavage of cTNT32 or HIV FS, despite both of these RNAs having structures loosely analogous to $CUG^{exp}$ (FIG. 5b, c). Thus, both similarly adopt stem-loop structures with internal loops within the stem, although obviously of different sequences. Differences between 6 and 9 were observed (FIG. 5) with the former cleaving $(CCUG)_8$ (SEQ ID NO: 11), the toxic RNA involved in myotonic dystrophy type 2 (DM2). In contrast, 9 showed no activity toward $(CCUG)_8$ (SEQ ID NO: 11). The ability to process the RNA directly parallels the corresponding ligand-RNA binding affinities. Thus, 1, which contains the acridine-triazine core of agent 6, complexes the $(CCUG)_6$ (SEQ ID NO: 12) and $(CUG)_n$ sequences. Likewise, 2 (the core of agent 9) complexes $(CUG)_n$ but showed no affinity toward $(CCUG)_8$ (SEQ ID NO: 11), cTNT32, or HIV FS. These data are consistent with the catalytic functionality being brought into proximity of the RNA through selective binding.

Biological Activities of Agents 5, 6, and 9 in DM1 Model Cells.

Figure 6:
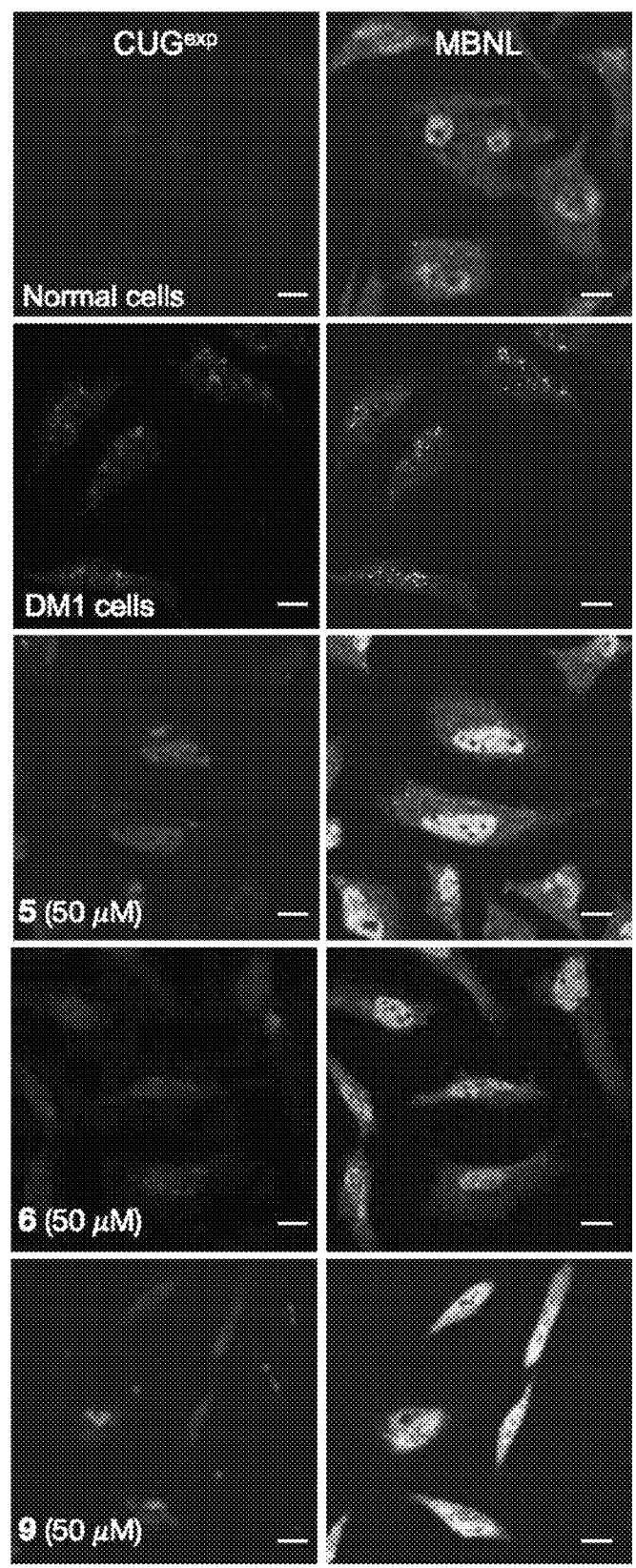
FIG. 6. Foci dispersion by ligands 5, 6, and 9. Ligands were incubated with DM1 model cells at 50 μM for 48 h. Cells were fixed and CUG$^{exp}$ stained with Cy3-(CAG)$_{10}$ (SEQ ID NO: 2), MBNL1 was probed with mouse anti-MBNL (EMD Millipore) followed by staining with goat anti-mouse Alexa® 647 secondary antibody (Thermo Scientific Pierce). The scale bar is 10 μm.

The ability of 5, 6, and 9 to disrupt the MBNL1-CUG interaction in cells was evaluated using model DM1 cells. Thus, HeLa cells were transfected with GFP-DT0 and GFP-DT960 plasmids that contain 0 or 960 interrupted CTG repeats, respectively, in exon 15 of a truncated DMPK gene. The plasmids express both GFP protein and $CUG^{exp}$ under the activation of doxycycline (Dox) with GFP being used as a marker for successful transfection and expression of the plasmids in the cells. Treatment of the DM1 model cells with ligands at 50 µM for 48 h was followed by analysis using confocal microscopy. As seen in the representative images of FIG. 6, each of the three agents inhibited nuclear foci formation and each led to dispersion of MBNL1 protein throughout the nucleus.

Because 9 is less toxic to HeLa cells than 5 and 6, it was selected for a splicing study of insulin receptor (IR) minigene. Splicing of IR minigene is mis-regulated with the abnormal exclusion of exon 11 because of the MBNL1 depletion in DM1 cells. DM1 model cells, in this case co-transfected with plasmids containing IR minigene and $(CTG)_{960}$ (SEQ ID NO: 13), were treated with 9 at 100 µM for 3 d leading to a 77% rescue of the IR splicing defect (FIG. 11).

Encouraged by the promising results from the in vitro cleavage and the ability of 5, 6, and 9 to enter cells and dissolve MBNL1-CUG nuclear foci, we performed experiments to study whether the agents could control the level of toxic $CUG^{exp}$ in cells using a reported protocol (Kalsotra et al., *Cell Rep.* 6, 336-345 (2014); Lee et al., *Proc. Natl. Acad. Sci. U.S.A.* 109, 4221-4226 (2012)). Two sets of cells, transfected with either GFP-DT0 or GFP-DT960 plasmids were incubated with 5, 6, or 9 for 3 d. The $CUG^{exp}$ mRNA level was determined by measuring the level of exon 15 upstream of the $CUG^{exp}$ relative to PABP mRNA as a control, normalizing the values to the levels measured from untreated cells. As seen in FIG. 7a, there was a 60-70% reduction in $CUG^{exp}$ levels in cells treated with 6 and 9 at 50 µM. Ligand 5 showed only a negligible change of $CUG^{exp}$ levels, although a longer incubation time of 5 and 7 d led to a significant decrease in the level of toxic $CUG^{exp}$ RNA (FIG. 12). Because of its lower toxicity, the dose dependence of 9 was examined by treating cells with four different concentrations ranging from 25 to 150 µM. As seen in FIG. 7b, agent 9 clearly regulates the cellular $CUG^{exp}$ mRNA levels in a dose-dependent manner.

Inhibition of $(CTG.CAG)_{74}$ (SEQ ID NOS 3-4, respectively) transcription by 5, 6, and 9 in vitro. As described above, simple ligands 1 and 3 did not alter cellular $CUG^{exp}$ mRNA levels, implicating the RNase-mimic activity of 5, 6, and 9 in their ability to suppress the toxic $CUG^{exp}$ mRNA in cells. Nonetheless, the additional ammonium groups in these agents might potentially increase their affinity for both CTG DNA and CUG RNA so we returned to examine the potential for inhibition of $CTG^{exp}$ transcription. The in vitro $(CTG.CAG)_{74}$ (SEQ ID NOS 3-4, respectively) transcription assays utilized a T7 promoter located in the upstream region of the repeats. Ligands 5 and 9 strongly inhibited the production of $CUG^{exp}$ and in a dose-dependent manner, whereas ligand 6 showed less inhibition. Control ligands 2, 7, and 10 had negligible effects on the transcription of $(CTG.CAG)_{74}$ (SEQ ID NOS 3-4, respectively) (FIG. 8 and FIG. 13).

To test the selectivity and potentially the target of the inhibition, we performed similar experiments with two separate control plasmids each lacking repeats (see Examples below for details). Ligand 6 showed negligible transcription inhibition at all tested concentrations, which ranged from 1 to 100 µM, whereas 9 strongly inhibited the transcription of the control plasmids at higher concentrations (i.e., 50 and 100 µM) (FIG. 13). However, 9 did show some selectivity in the inhibition with only 30% inhibition of the control plasmids observed at 10 µM, whereas the plasmid containing (CTG.CAG)$_{74}$ (SEQ ID NOS 3-4, respectively) still showed ca. 80% inhibition (FIG. 8b).

The lack of binding affinity shown by 2 toward d(CTG)$_{12}$ (SEQ ID NO: 14), d(CAG)$_{12}$ (SEQ ID NO: 15), and d(CTG.CAG)$_{12}$ (SEQ ID NOS 14-15, respectively) (Table 1), combined with the transcription inhibition data collected for 9 supports the notion that ammonium groups increase its affinity for CTG$^{exp}$. To directly assess the DNA-targeting ability of 9, ITC experiments were performed with oligonucleotide analogs of the various trinucleotide repeat sequences (Table 1). In contrast to 1, 9 showed comparable binding affinities toward d(CTG)$_{12}$ (SEQ ID NO: 14) and (CUG)$_{12}$ (SEQ ID NO: 16) hairpin structures. This supports the idea that 9 inhibits the transcription of CTG$^{exp}$ by stabilizing its hairpin structure. Indeed, no strong binding was detected for d(CAG)$_{12}$ (SEQ ID NO: 15) or d(CTG.CAG)$_{12}$ (SEQ ID NOS 14-15, respectively) (Table 1). The in vitro transcription experiment using (CTG□CAG)$_{74}$ (SEQ ID NOS 3-4, respectively) and compounds 2, 5-7, and 9 was repeated but with (CUG)$_{16}$ (SEQ ID NO: 1) added as a competitor. In each case, the transcription inhibition of ligands was reduced, particularly for 6 (FIG. 14).

Ligand 9 Suppresses Neurodegeneration, Regulates CUG$^{exp}$ mRNA Levels, and Reverses the Disease Phenotype in DM1 Drosophila.

Figure 15C:
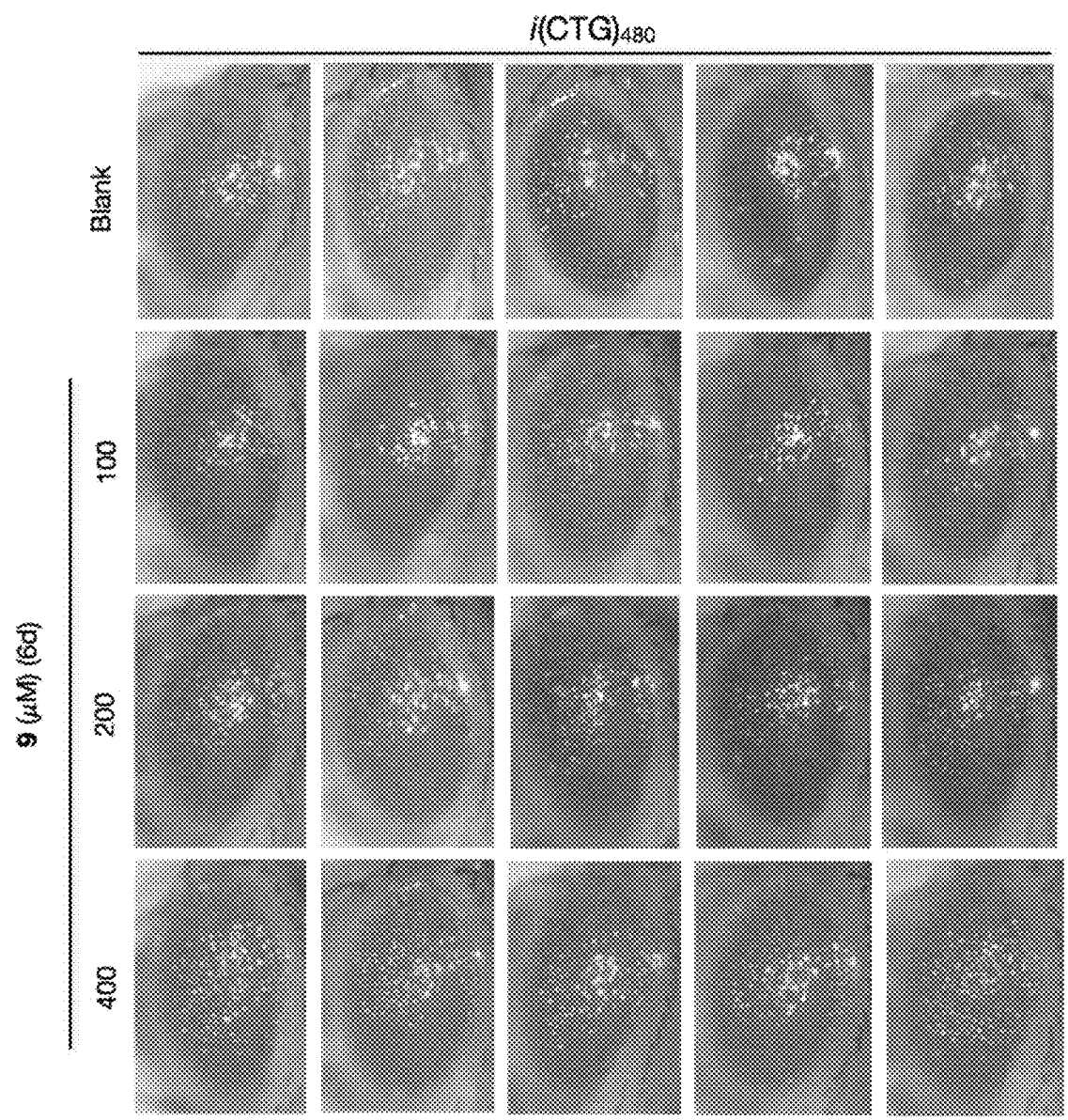

The data presented above indicate that 9 is able to engage each of three small molecule intervention pathways outlined in FIG. 1b and it was found further to be relatively non-toxic. For these reasons, it was selected for in vivo testing in a DM1 Drosophila model, specifically transgenic flies that express an interrupted (CTG)$_{480}$ (SEQ ID NO: 6) sequence (i(CTG)$_{480}$ (SEQ ID NO: 6)). The flies exhibit severe neurodegeneration and manifest a number of disease symptoms including the well-characterized glossy and rough-eye phenotype that can be easily observed microscopically (FIG. 9a). Treatment of the DM1 flies with ligand 9 improved the neurodegenerative phenotype in a dose-dependent fashion. Particularly striking is a significant reduction in glossiness and a better-defined eye shape clearly observed after a 6 d treatment regimen (FIG. 9a and FIG. 15). As we previously reported, control ligand 2 also showed reversal of the disease phenotype but less effectively.

These DM1 Drosophila exhibit other phenotypes, including impaired locomotion. To test the abilities of 2 and 9 to improve the locomotor behavior of Drosophila larvae, we used crawling assays (Nichols et al., J. Vis. Exp. 61, e3795 (2012); Lanson et al., Hum. Mol. Genet. 20, 2510-2523 (2011); Batlevi et al., Proc. Natl. Acad. Sci. U.S.A. 107, 742-747 (2010)). Untreated larvae having i(CUG)$_{60}$ (SEQ ID NO: 8) do not show the phenotype and crawled with an average speed of ca. 13 lines/min, which is considered baseline locomotion. Those expressing i(CUG)$_{480}$ (SEQ ID NO: 17) crossed only 9 lines/min (FIG. 9b). Larvae that were treated with the highest doses of 2 and 9 (400 µM) showed significant improvement in locomotion with an average crawling speed approaching the normal baseline level of ca. 13 lines/min. Importantly, the phenotypic improvement with both compounds was dose-dependent and 9 in all cases provided greater phenotypic reversal than did 2. Thus, with doses ranging from 100 to 400 µM, 9 exhibited between 38% and 89% recovery of normal locomotor behavior, whereas 2 showed only between 14% and 83% recovery (FIG. 9b).

Because 9 regulated the level of toxic CUG$^{exp}$ in cells, we performed experiments to determine whether the same activity was present in DM1 flies. SV40 terminator mRNA is downstream from the i(CUG)$_{60}$ (SEQ ID NO: 8) and i(CUG)$_{480}$ (SEQ ID NO: 17) regions (FIG. 9c). Thus, its amplification using specific primers (detailed in the Examples section below) is directly correlated with CUG$^{exp}$ mRNA levels. The SV40 mRNA was expressed approximately equally in larvae bearing either i(CUG)$_{60}$ (SEQ ID NO: 8) or i(CUG)$_{480}$ (SEQ ID NO: 17) (FIG. 9d). Treatment with 2 and 9 at 400 µM showed no change in SV40 mRNA levels measured in larvae having i(CUG)$_{60}$ (SEQ ID NO: 8). In contrast, 9 reduced by ca. 40-60% the SV40 mRNA levels in the i(CUG)$_{480}$ (SEQ ID NO: 17) larvae whereas 2 did not. This result demonstrates the in vivo selectivity of 9 toward larvae expressing disease-length CUG trinucleotide repeats.

Discussion.

The "holy grail" of DM1 therapeutic strategies would involve contraction of CTG$^{exp}$ to nondisease lengths. Such a process could represent a cure for the disease. This is a particularly difficult challenge because multiple processes cause the expansion and their detailed mechanisms are not known. For this reason, drug discovery efforts to date have largely focused on the toxic CUG$^{exp}$ transcript and its gain of function mechanism. A number of single-target small molecules are known that selectively recognize CUG$^{exp}$ and liberate sequestered MBNL1. However, recent reports indicate a more complex disease pathobiology suggesting that binding CUG$^{exp}$ may not be enough to reverse all disease pathways. Thus, efforts to destroy the toxic RNA transcript or inhibit its formation have particular appeal. Three reported examples of agents that control CUG$^{exp}$ levels include antisense agents that induced CUG$^{exp}$ cleavage via an RNase H dependent manner, small molecules that degraded CUG$^{exp}$ through a photo-induced cleavage (Guan and Disney, Angew. Chem. Int. Ed. 52, 1462-1465 (2012)), and (CTG.CAG)$_n$ transcription inhibitors (Coonrod et al., ACS Chem. Biol. 8, 2528-2537 (2013)).

The efforts described herein sought a single small molecule agent that might intervene in multiple DM1 disease pathways. We discovered three agents, 5, 6, and 9 that, indeed, operate in three distinct ways. Each shows RNase A-like activity in selectively cleaving (CUG)$_{16}$ (SEQ ID NO: 1) in vitro, and each inhibits both the in vitro transcription of CTG$^{exp}$, and the sequestration of MBNL1 into nuclear foci in DM1 model cell culture. Not all of the compounds performed equally well at each of these tasks. For example, 6 and 9 cleaved (CUG)$_{16}$ (SEQ ID NO: 1) more rapidly than 5 and both fully inhibited nuclear foci formation, whereas 5 was not quite as effective. As a CTG$^{exp}$ transcription inhibitor, 9 was most effective, but it was less selective than 6. Interestingly, the least effective transcription inhibitor, 6, was most effective at suppressing cellular levels of (CUG)$_{960}$ (SEQ ID NO: 7). Although this might suggest that the RNA cleaving activity is most important, the cellular suppression of (CUG)$_{960}$ (SEQ ID NO: 7) over the 3 d period appears to well out-pace the in vitro RNA cleavage rates. The latter are quite slow even at high compound concentration. It is possible that one or more RNA nicks activate an endogenous RNase or it may just reflect the complexity of the cell where (CUG)$_{960}$ (SEQ ID NO: 7) suppression will depend on many factors, including cell permeability, and the effectiveness of the three separate targeting activities in the complex environment of the cell.

Taking into account all of the results and particularly the low cytotoxicity exhibited by 9, it was considered the most promising candidate for in vivo studies. In a DM1 *Drosophila* model, 9 was found to rescue the neurodegeneration, thereby significantly reversing both the rough-eye phenotype and the larvae locomotor function. To the best of our knowledge, 9 is the first small molecule to control the level of CUG$^{exp}$ in a DM1 model organism. The reduction in the toxic RNA levels supports the role of its multi-target ability observed in earlier studies. It was especially noteworthy that control compound 2 shows no suppression of the CUG$^{exp}$ levels.

None of the compounds described herein are able to recognize or affect the (CAG)$^{exp}$ transcript so it is able to undergo RAN translation. It is also the case that agents such as 5, 6, and 9 that nick RNA and may be acting as transcription inhibitors will have to exhibit a very high level of selectivity to avoid undesirable off-target activity. Indeed, in the transcription assays with 9, some inhibition was observed with the control sequences. The repeating nature of the trinucleotide repeat target means that a bi- or polyvalent strategy can easily amplify selective targeting. Most significantly, we have demonstrated the first rational multi-target drug discovery effort that has led to three small molecules that intervene in three separate pathobiological steps in DM1, including showing enhanced phenotypic reversal in a DM1 *Drosophila* model.

General Synthetic Methods

The invention also relates to methods of making the compounds and compositions of the invention. The compounds and compositions can be prepared by applicable techniques of organic synthesis. Many such techniques are well known in the art. For example, many techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5th Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis*, Second Edition, Cary and Sundberg (1983); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of compounds of the invention are provided below. These methods are intended to illustrate the nature of such preparations and are not intended to limit the scope of applicable methods. Generally, reaction conditions such as temperature, reaction time, solvents, work-up procedures, and the like, will be those common in the art for the particular reaction to be performed. The cited reference materials, together with the materials cited therein, contain detailed descriptions of such conditions. Typically the temperatures will be −100° C. to 200° C., solvents will be aprotic or protic, depending on the conditions required, and reaction times will be 1 minute to 2 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions the temperature is frequently reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are known in the art and can be applied when applicable.

Protecting Groups. The term "protecting group" refers to any group that, when bound to a hydroxyl, nitrogen, or other heteroatom, prevents undesired reactions from occurring at the sight of the heteroatom, and which group can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)), and any other group that can be introduced chemically onto a hydroxyl functionality and later selectively removed either by chemical or enzymatic methods in mild conditions compatible with the nature of the product. The $R^1$ and $R^2$ groups of Formula I can also be protecting groups, as described herein.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

In general, modifications to the compounds and formulas described herein can be made according to organic synthesis techniques known to those of skill in the art and/or according to the synthetic schemes provided herein. Where desired, synthesis of a compound can begin with commercially available chemicals, from compounds described in the chemical literature, or from products of the reactions and methods described herein. Commercially available compounds may be obtained from standard commercial sources including Acros Organics (Pittsburgh, Pa.), Aldrich Chemical (Milwaukee Wis., including Sigma Chemical and Fluka), Aurora Fine Chemicals (San Diego, Calif.), Acorn Pharmatech (Redwood City, Calif.), Atomax Chemical Co. (Shenzhen, China), Eastman Organic Chemicals, Eastman Kodak Company (Rochester N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), Wako Chemicals USA, Inc. (Richmond, Va.), and the like. Other starting materials and intermediates can be readily prepared in one to a few steps from commercially available starting materials using standard synthetic transformations familiar to those of skill in the art.

Salts and Solvates

The compounds described herein can be purified and isolated in their free-base or free-acid forms or they can be isolated in their salt forms, for example, hydrohalide salts, including salts with two, three, four or more equivalents of the hydrohalide, as appropriate.

Pharmaceutically acceptable salts of compounds described herein are within the scope of the invention and include acid or base addition salts which retain the desired pharmacological activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. $Na^+$, $Li^+$, $K^+$, $ca^{2+}$, $Mg^{2+}$, $Zn^{2+}$) ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free-base or free-acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Examples of suitable salts of the compounds described herein include their hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salt, or a similar salt.

When compounds described herein contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as salts derived from organic acids like acetic, behenic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as in solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates.

Pharmaceutical Formulations

The following describes information relevant to pharmaceutical and pharmacological embodiments and is further supplemented by information in the art available to one of ordinary skill. The exact formulation, route of administration and dosage can be chosen by an individual physician in view of a patient's condition (see e.g., Fingl et al., in *The Pharmacological Basis of Therapeutics,* 1975, Ch. 1).

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

A compound may be combined with different types of carriers depending on whether it is to be administered in solid, liquid or aerosol form, and whether it need to be sterile for such routes of administration as injection. Compounds and compositions described herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, *Remington's Pharmaceutical Sciences*, 18th Ed. Mack Printing Company, 1990).

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Compound Preparation

Synthetic Procedures for Ligand Preparation.

Unless otherwise noted, $^1$H and $^{13}$C NMR spectra were recorded on a 500 MHz Varian Unity Inova spectrometer. All NMR measurements were carried out at ambient temperature. Chemical shifts are in parts per million (ppm), relative to the residual solvent peaks. Coupling constants (J) were reported in Hertz. Electrospray ionization mass spectra (ESI-MS) was used for mass spectrometry analysis. High performance liquid chromatography (HPLC) was performed by a Dynamax SD-200 system with a UV detector set at 254 nm using an Alltech Denali C-18 column (250×10 mm) with a dual solvent system of 50% MeOH: 50% H$_2$O with or without 0.1% TFA.

Scheme 1. Preparation of ligands 5 and 6

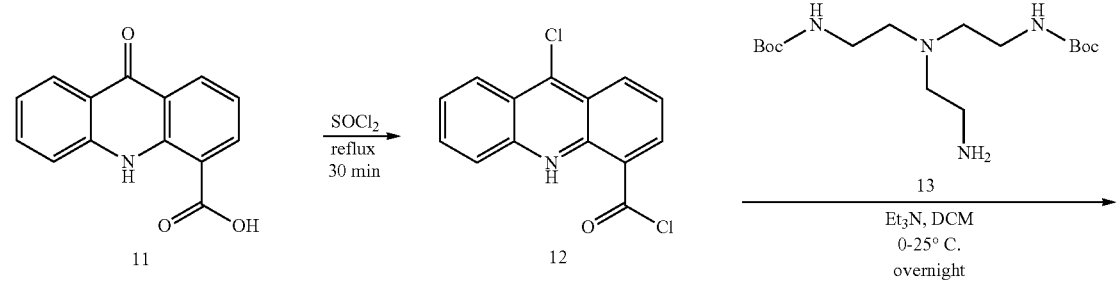

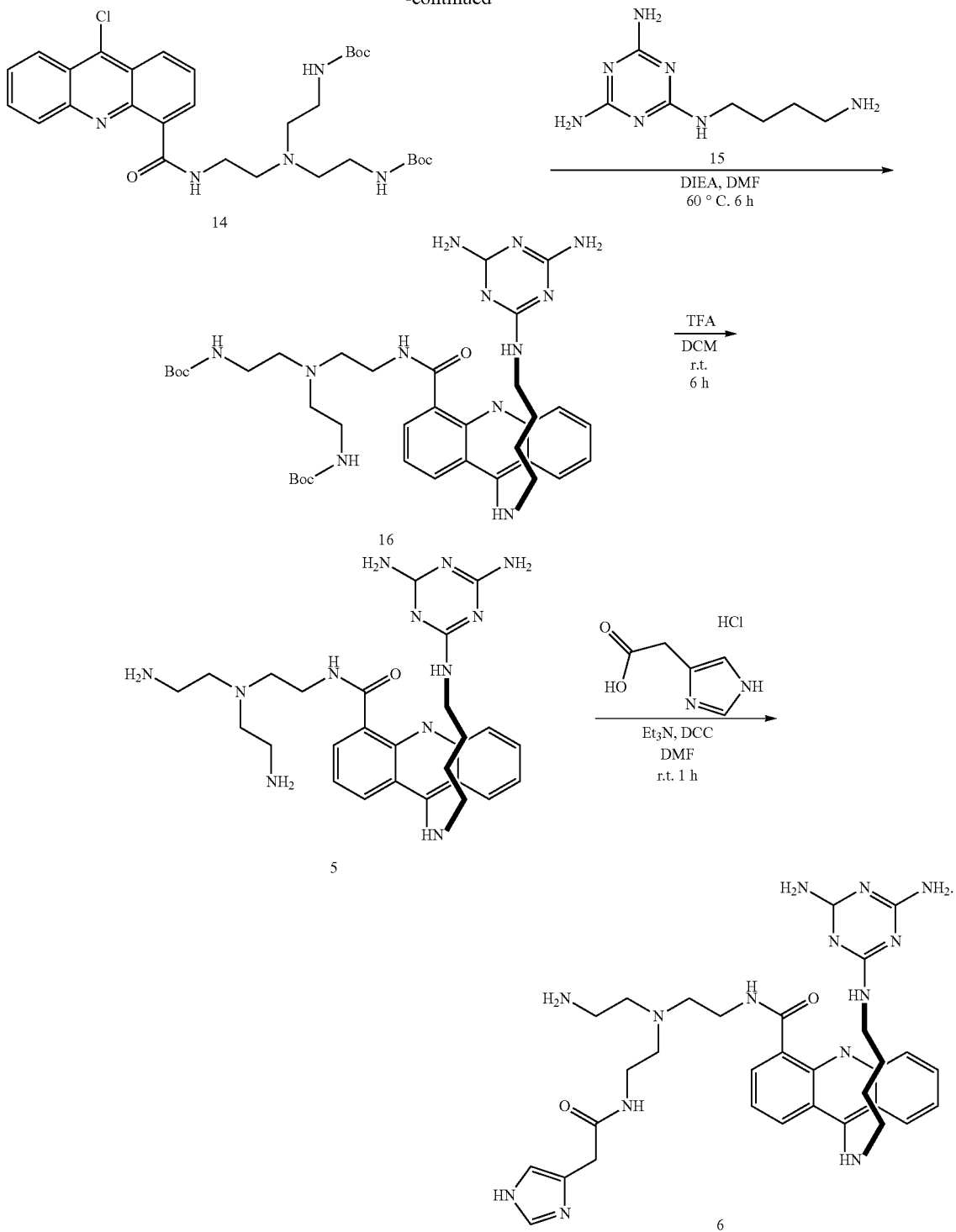

Compounds 12, 14, and 16 were synthesized by following the procedures (see also Jahromi et al., *ACS Chem. Biol.* 8, 1037-1043 (2013)).

Compound 14: To a 35 mL round-bottomed flask containing 500 mg (2.1 mmol) of compound 9-oxo-9,10-dihydroacridine-4-carboxylic acid (11) was added 5 mL (68.9 mmol) of SOCl$_2$ using a syringe and 4 drops of anhydrous DMF. The reaction mixture was refluxed for 1 h. Unreacted SOCl$_2$ was removed azeotropically using DCM. The orange solid containing 12 was dried under high vacuum and used for the next reaction without further purification.

The crude product containing 12 was dissolved in 10 mL of anhydrous DCM and cooled down in an ice bath. The pH of the solution was adjusted to 11 using anhydrous Et$_3$N. The solution of 809 mg (2.3 mmol) of 13 in 5 mL of anhydrous DCM was added slowly to the reaction mixture. The reaction was slowly warmed up to room temperature and stirred overnight. The reaction was monitored using TLC with a mixture of ethyl acetate:hexane=8:2. Dichloromethane was removed using a rotary evaporator. The obtained orange solid was dissolved in 5 mL of ethyl acetate and purified by a silica column chromatography using a gradient mixture of ethyl acetate:hexane from 2:8 to 8:2, giving compound 14 as a yellow solid (280 mg, 23%). $^1$H NMR (DMSO-$d_6$): δ 11.11 (br s, NHCO, 1H), 8.76 (dd, ArH, 1H), 8.62 (dd, ArH, 1H), 8.45 (d, ArH, 1H), 8.34 (d, ArH, 1H), 8.03 (dt, ArH, 1H), 7.86 (m, ArH, 2H), 3.60 (p, $CH_2$, 2H), 3.05 (p, $CH_2$, 4H), 2.81 (t, $CH_2$, 2H), 2.66 (p, $CH_2$, 4H), 1.15 (br s, $CH_3$, 18H).

Compound 16: To a 50 mL round-bottomed flask containing 280 mg (0.5 mmol) of 14 in 20 mL of anhydrous DMF was added 109 mg (0.6 mmol) of $N^2$-(4-aminobutyl)-1,3,5-triazine-2,4,6-triamine (15) and 0.19 mL (1.1 mmol) of DIPEA. The reaction was stirred at 60° C. for 6 h. The solvent was removed using vacuum, giving an orange solid. The crude solid was dissolved in 5 mL of DCM and purified by alumina column chromatography using a mixture of DCM:MeOH=95:5, giving compound 16 as an orange solid (240 mg, 67%). $^1$H NMR (DMSO-$d_6$): δ 8.60 (d, ArH, 1H), 8.55 (d, ArH, 1H), 8.42 (d, ArH, 1H), 7.97 (d, ArH, 1H), 7.75 (t, ArH, 1H), 7.53 (bt, NHCO, 1H), 7.44-7.38 (m, ArH, 2), 6.63 (bs, $NH_2$, 2), 6.43 (bt, $NH_2$, 2), 6.02 (bs, $NH_2$, 2), 5.87 (bs, $NH_2$, 2), 3.87 (bp, $CH_2$, 2H), 3.54 (bp, $CH_2$, 2H), 3.15 (p, $CH_2$, 2H), 3.03 (bs, $CH_2$, 4H), 2.76 (bt, $CH_2$, 2H), 2.65 (bt, $CH_2$, 4H), 1.76 (bp, $CH_2$, 2H), 1.51 (bp, $CH_2$, 2H), 1.21 (bs, $CH_3$, 18H).

Ligand 5.

To a 50 mL round-bottomed flask containing 280 mg (0.5 mmol) of di-tert-butyl (((2-(9-chloroacridine-4-carboxamido)ethyl)azanediyl)bis(ethane-2,1-diyl))dicarbamate in 20 mL of dry DMF was added 109 mg (0.6 mmol) of $N^2$-(4-aminobutyl)-1,3,5-triazine-2,4,6-triamine and 0.19 mL (1.1 mmol) of DIPEA. The reaction was stirred at 60° C. for 6 h. DMF was removed using vacuum, obtained an orange solid. The crude solid was dissolved in 5 mL of dichloromethane and subjected to the Alumina column. The desired product was purified by chromatography with a solvent DCM:MeOH=95:5, giving the desired compound as an orange solid (240 mg, 67%).

To a 100 mL round-bottomed flask containing 240 mg (0.3 mmol) of the orange solid in 40 mL of dichloromethane was added 10 mL (130.7 mmol) of trifluoroacetic acid. The reaction was stirred at room temperature for 6 h. The solvent was removed using a rotary evaporator and dried under vacuum to give compound 5 in a form of TFA salt, as a yellow solid (100%). $^1$H NMR ($D_2O$) δ 8.40 (br d, ArH, 1H, J=8.5), 8.22 (br d, ArH, 1H, J=8.5), 8.12 (dd, ArH, 1H, J=1.5, 6), 7.81 (td, ArH, 1H, J=1.5, 7.5), 7.66 (d, ArH, 1H, J=7.5), 7.41 (br t, ArH, 2H, J=8, 8.5), 4.05 (br t, $CH_2$, 2H, J=6.5), 3.55 (t, $CH_2$, 2H, J=7), 3.15 (br t, $CH_2$, 2H, J=6, 6.5), 3.10 (br t, $CH_2$, 4H, J=6.5), 2.99 (br t, $CH_2$, 4H, J=6.5), 2.93 (br t, $CH_2$, 2H, J=7), 1.85 (br q, $CH_2$, 2H, J=6), 1.58 (br q, $CH_2$, 2H, J=6, 6.5, 7). ESI-MS (m/z) calculated for $[M+H]^+$:547.3. found 547.3 [M+H].

Ligand 6.

To a 20 mL round-bottomed flask containing 200 mg (0.4 mmol) of compound 5 in 5 mL DMF was added $Et_3N$ to pH 7. The solution of 101 mg (0.6 mmol) of imidazole acetic acid and 129 mg (0.6 mmol) of DCC in 5 mL DMF was added to the above solution. The reaction was stirred at room temperature overnight. The solvent was removed under vacuum. The crude product was purified using the reversed phase C18 column on a CombiFlash system ($MeOH:H_2O$=0:100 to 50:50) to afford compound 6 as a yellow solid (15 mg, 12%). $^1$H NMR ($D_2O$) δ 8.49 (m, ArH, 1H), 8.35 (br s, ArH, 1H), 8.35 (br s, ArH, 1H,), 8.25 (br d, ArH, 1H, J=8), 7.94 (br t, ArH, 1H, J=8), 7.78 (br t, ArH, 1H, J=8.5), 7.54 (br t, ArH, 2H, J=8), 7.12 (s, CH, 1H), 4.19 (br t, $CH_2$, 2H, J=6.5, 7), 3.68 (br t, $CH_2$, 2H, J=3.5), 3.46 (br s, $CH_2$, 2H, J=6.5), 3.27 (m, $CH_2$, 2H), 3.16 (m, $CH_2$, 4H), 3.09 (m, $CH_2$, 4H), 2.95 (br t, $CH_2$, 2H), 2.00 (br q, $CH_2$, 2H, J=7, 8), 1.72 (br q, $CH_2$, 2H, J=7, 8). ESI-MS (m/z) calculated for $[M+H]^+$: 655.4. found 655.8 $[M+H]^+$, 328.5 $[M+2H]^{2+}$.

Scheme 2. Preparation of ligand 8

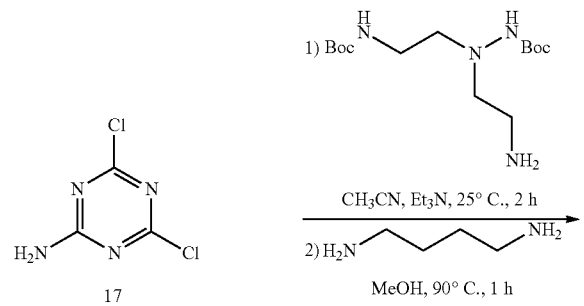

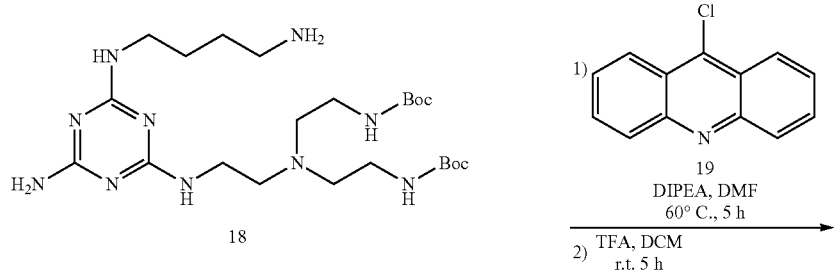

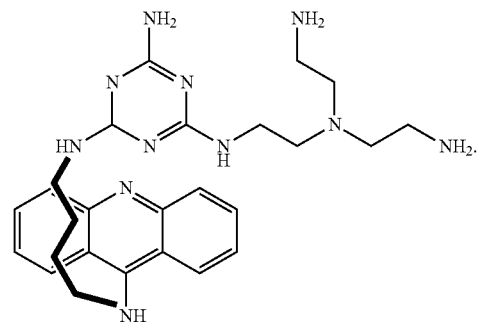

8

Compound 18: To a 50 mL round-bottomed flask containing 690 mg (4.2 mmol) of compound 17 was added 10 mL of acetonitrile and 0.7 mL (5.0 mmol) of triethylamine. The suspension was stirred at room temperature for 5 min. To the reaction flask was added 1.7 g (4.9 mmol) of 13 at once, giving a clear solution. The reaction was stirred at room temperature for 2 h. Acetonitrile was removed using a rotary evaporator. The obtained solid was dissolved in 30 mL of MeOH. To the resulting solution was added 2.0 mL (19.9 mmol) of 1,4-diaminobutane at once. The reaction was heated to 90° C., and stirred for 1 h. Methanol and the excess amount of diaminobutane were removed by a rotary evaporator. The crude was purified by silica gel column chromatography with a mixture of $CH_2Cl_2$/MeOH/$NH_4OH$=90/9/1. Fractions containing product were combined and concentrated to give 1.3 g (59%) of compound 18 as a white solid. $^1$H NMR (DMSO-$d_6$): δ 6.75 (br s, NHBoc, 2H), 6.53-5.81 (m, ArH, 4H), 3.19-3.14 (m, $CH_2$, 4H), 2.97 (br s, $CH_2$, 4H), 2.56-2.53 (t, $CH_2$, 2H, J=6.9), 2.46-2.44 (t, $CH_2$, 6H, J=6.5), 1.49-1.30 (m, $CH_2$, 4H), 1.37 (br s, $CH_3$, 18H). ESI-MS (m/z) calculated for [M+H]$^+$:527.4. found 527.2.

Ligand 8: To a 100 mL 24/40 round-bottomed flask was added 850 mg (1.6 mmol) of melamine 18 and 420 mg (2.0 mmol) of acridine 19. The mixture was dissolved in 20 mL of DMF. To the resulting yellow solution was added 0.3 mL (1.7 mmol) of DIPEA. The mixture was stirred at 60° C. for 5 h. The solvent was removed using a rotary evaporator. The crude was purified by $Al_2O_3$ (activated, basic) column chromatography using DCM/MeOH mixture (gradient from 100/0 to 97/3 (v/v)). The fractions containing products were combined and concentrated using a rotary evaporator. The yellow solid was dissolved in a mixture of 25 mL of TFA and 25 mL of DCM. The solution was stirred at room temperature for 5 h. The reaction was concentrated using a rotary evaporator, and dried overnight under high vacuum to give 876 mg (51%) of compound 8 as a yellow solid. $^1$H-NMR (500 MHz, $CD_3OD$-$d_4$): δ 8.51-8.49 (m, 2H, ArH), 7.96-7.94 (m, 2H, ArH), 7.82-7.80 (m, ArH, 2H), 7.55 (t, ArH, 2H, J=7.9), 4.22-4.21 (m, NHCH$_2$, 2H), 3.49-3.45 (m, NHCH$_2$, 4H), 3.10-3.05 (m, NH$_2$CH$_2$, 4H), 2.87-2.71 (m, NCH$_2$, 6H), 2.09-2.02 (m, CH$_2$CH$_2$, 2H), 1.82-1.74 (m, CH$_2$CH$_2$, 2H). ESI-MS (m/z) calculated for [M+H]$^+$:504.3. found 504.3.

Scheme 3. Preparation of ligand 4

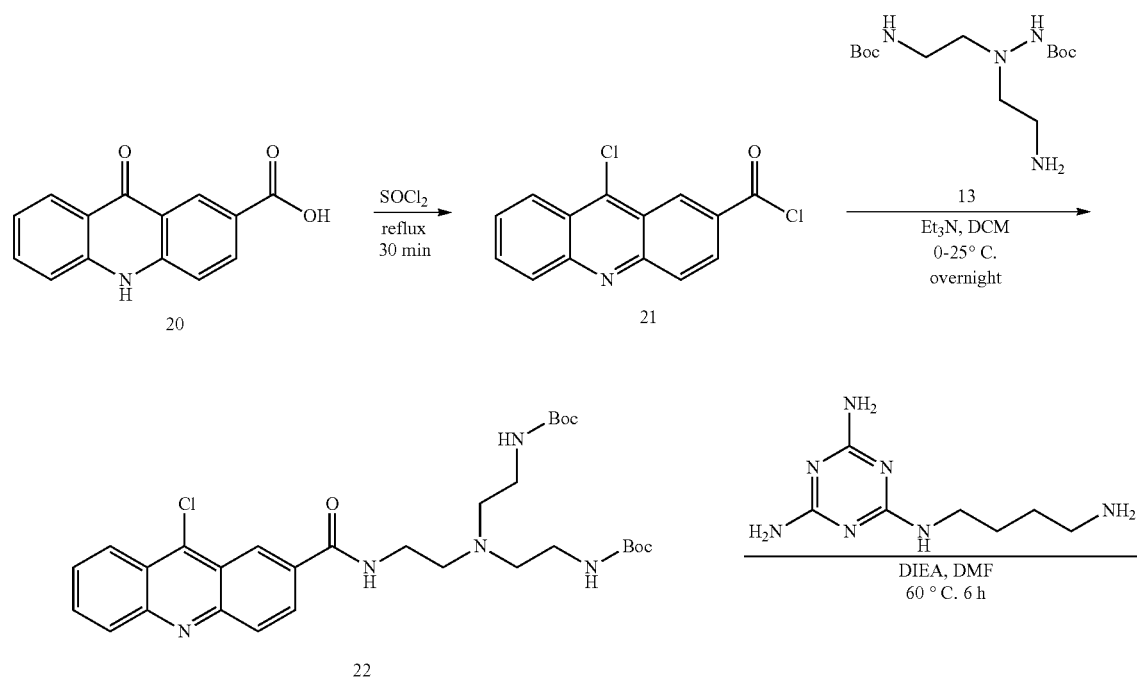

-continued

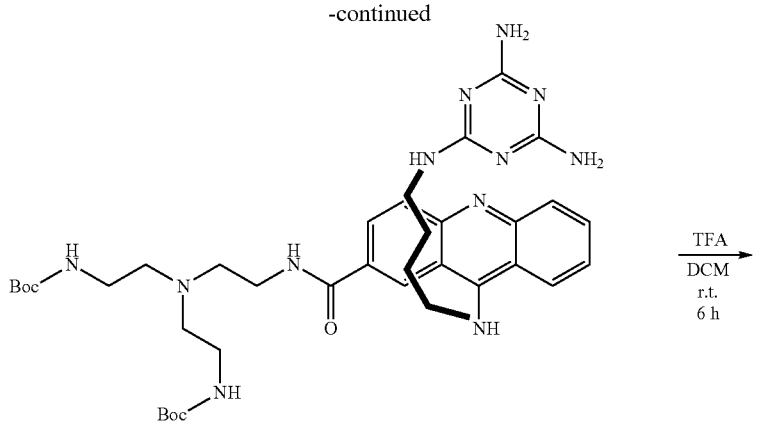

23

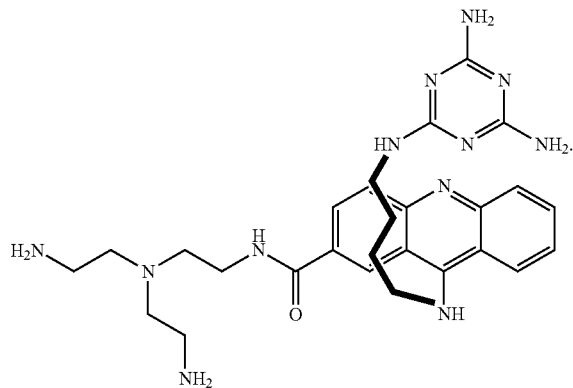

4

Compound 22: To a 35 mL round-bottomed flask containing 300 mg (1.3 mmol) of 20 synthesized followed the reported protocol (Jahromi et al., *J. Med. Chem.* 56, 9471-9481 (2013)) was added 2 mL (27.6 mmol) of $SOCl_2$ using a syringe and 8 drops of dry DMF. The reaction mixture was refluxed for 1 h. The unreacted $SOCl_2$ were removed azeotropically using DCM. The crude orange product containing 21 was dried under high vacuum and used for the next reaction without further purification.

The crude product containing 21 was dissolved in 10 mL of anhydrous DCM and cooled down in an ice bath. The pH of the solution was adjusted to 11 using anhydrous $Et_3N$. The solution of 400 mg (1.2 mmol) of 13 in 5 mL of anhydrous DCM was added slowly to the reaction mixture. The reaction was slowly warmed up to room temperature and stirred overnight. The reaction was monitored using TLC with a mixture of ethyl acetate:hexane=8:2. Dichloromethane was removed using a rotary evaporator. The obtained orange solid was dissolved in 5 mL of ethyl acetate and purified by silica column chromatography using a gradient mixture of ethyl acetate:hexane from 2:8 to 8:2, giving compound 22 as a yellow solid (300 mg, 25%). $^1H$ NMR (DMSO-$d_6$): δ 8.90 (t, J=3.3, 1H), 8.47-8.42 (m, 1H), 8.29-8.24 (m, 2H), 7.99 (ddd, J=8.4, 6.6, 1.4, 1H), 7.82 (ddd, J=8.9, 6.6, 1.2, 1H), 6.69 (t, J=5.7, 1H), 3.38 (q, J=6.5, 2H), 2.99 (q, J=6.7, 6.2, 4H), 2.66 (t, J=6.8, 2H), 2.52 (t, J=6.8, 4H), 1.32 (s, 18H).

Compound 4: To a 50 mL round bottom flask containing 270 mg (0.5 mmol) of compound 22 in 20 mL of anhydrous DMF was added 105 mg (0.5 mmoL) of $N^2$-(4-aminobutyl)-1,3,5-triazine-2,4,6-triamine (15) and 0.184 mL (1.1 mmol) of DIPEA. The reaction was stirred at 60° C. for 6 h. DMF was removed using vacuum, affording an orange solid. The crude solid was dissolved in 5 mL of DCM and purified by alumina column chromatography with a mixture of DCM:MeOH=95:5, giving compound 23 as an orange solid (260 mg, 72%). To a 100 mL round bottom flask containing 260 mg of compound 23 in 20 mL of DCM was added 10 mL of TFA. The reaction was stirred at room temperature for 6 h. The solvent was removed using a rotary evaporator and dried under vacuum to give compound 4 as a yellow TFA salt (100%). $^1H$ NMR ($D_2O$): 8.70 (t, J=2.6, 1H), 8.22 (s, 1H), 8.04 (dq, J=8.9, 1.7, 1H), 7.83-7.77 (m, 1H), 7.60 (t, J=6.9, 2H), 7.40 (s, 1H), 4.13-4.07 (m, 2H), 3.54 (t, J=6.9, 2H), 3.17 (q, J=1.9, 1.4, 2H), 3.11 (d, J=6.4, 4H), 3.04 (s, 4H), 2.96 (s, 2H), 1.88 (s, 2H), 1.60 (s, 2H). ESI-MS (m/z) calculated for $[M+H]^+$: 547.3. found 547.3.

Scheme 4. Preparation of ligand 9

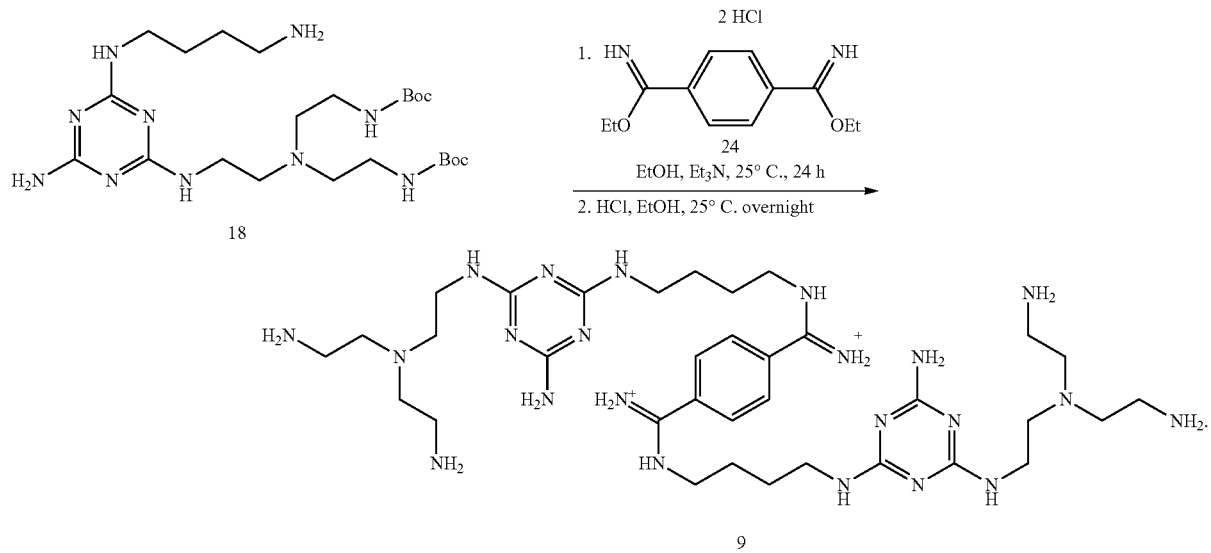

Ligand 9. To a 100 mL oven-dried round-bottomed flask was added 250 mg (0.9 mmol) of diethyl terephthalimidate hydrochloride. The white solid was dissolved in 15 mL of anhydrous ethanol. The resulting suspension was added 0.3 mL (2.2 mmol) of anhydrous Et$_3$N. To the obtaining clear solution was added 1.0 g (1.9 mmol) of di-tert-butyl (((2-((4-amino-6-((4-aminobutyl)amino)-1,3,5-triazin-2-yl)amino)ethyl)azanediyl)bis(ethane-2,1-diyl))dicarbamate at once. The resulting suspension was stirred at room temperature for 1 d. The solvent was removed using a rotary evaporator. The crude was dissolved in 20 mL of 2N ethanolic solution of HCl. The reaction was stirred at room temperature overnight. Ethanol was removed using a rotary evaporator. The crude was purified by Sephadex CM25 column chromatography with aqueous solution of NH$_4$HCO$_3$ from 0.1 M to 1.0 M. Fractions containing products were combined, concentrated at 60° C. using a rotary evaporator. The solid was dissolved in 80 mL of 0.1M aqueous solution of HCl. The resulting solution was concentrated using a rotary evaporator to give 0.39 g (40%) of compound 9 as a white HCl salt. $^1$H NMR (DMSO-d$_6$): δ 10.27 (br s, NH, 2H), 9.80 br rs, NH, 2H), 9.46-9.41 (m, NH, 2H), 8.42-7.90 (m, ArH, 8H), 8.00 (s, ArH, 4H), 3.87 (br s, NH$_2$, 8H), 3.54-3.35 (m, CH$_2$, 12H), 2.96 (br s, CH$_2$, 8H), 2.76-2.62 (m, CH$_2$, 12H), 1.71-1.64 (m, CH$_2$, 8H). ESI-MS (m/z) calculated for [M+H]$^+$: 781.6. found 781.6.

Example 2

RNA Cleavage Experiments and Related Analyses

RNA was purchased from Integrated DNA Technologies (Coralville, Iowa) and GE Dharmacon (Lafayette, Colo.). RNA samples were dissolved in THE Ambion® RNA storage solution and stored at −20° C. Concentrations of the RNA solutions were determined by performing absorbance measurements at 25° C. on a Shimadzu UV-2501PC spectrophotometer. The concentration of the double-stranded RNA was calculated using Beer's law with the extinction coefficient at 260 nm provided by the supplier.

RNA Cleavage Experiments.

RNA was fast folded at 95° C. for 5 min, followed by placing in ice for 10 min. RNA with a final concentration of 100 nM was incubated with cleaving agents 100 μM (in screening assays) and with ligand 9 at different concentrations (5, 10, 50, 100 μM). The cleaving buffer was 50 mM Tris buffer (pH 7.4) containing 150 mM NaCl and 2 mM MgCl$_2$. The final volume of the reaction mixture was 10 μL. The reaction was quenched by adding 8 μL of 8 M urea and 2 μL of RNA loading dye followed by heating at 95° C. for 5 min. The mixture was separated on a 20% RNA denaturing gel. For non-labeled RNA, the gel was stained with EtBr and observed under UV. For TAMRA-(CUG)$_{16}$ (SEQ ID NO: 1), the gel was scanned using Typhoon instrument in the Biotech Center Lab (Noyes Laboratory, School of Chemical Sciences, University of Illinois, Urbana, Ill.). The images were worked up using ImageJ software (NIH). Foci dispersion and IR splicing experiments were followed the reported protocols (Wong et al., J. Am. Chem. Soc. 136, 6355-6361 (2014)).

Cellular mRNA Level Study with Dox Treatment.

Approximately 50,000 HeLa cells were plated on a 12-well plate in DMEM media supplemented with high glucose, L-glutamine and no antibiotics a day before transfection. HeLa cells were transfected with 1 μg of GFP-DT0 or GFP-DT960 plasmids using Lipofectamine (Life Technologies) followed the recommended protocol. After 4 h, the transfection cocktail was replaced with the growing media and cells were treated with 1 μg of Dox. Ligands were treated at the same time at desired concentrations for 3 d. Cells were checked under fluorescence microscopy for GFP signal as a marker of successful transfection and then harvested. Total mRNA was isolated using E.Z.N.A.® total RNA kit I (Omega). Approximately 1.5 μg of total mRNA was subjected to DNase treatment to remove all DNA contaminant. cDNA synthesized using Iscript cDNA synthesis kit (Bio-Rad) was used as template in real time-PCR using SYBR® master mix (Applied Biosystem). The results from real time-PRC experiments were analyzed using the ΔΔCt method. The mRNA levels of exon 15 upstream of CUG$^{exp}$ were measured relative to PABP mRNA levels. The different in expression levels of RNA transcript between treated GFP-DT0 and GFP-DT960 samples were compared with the one in untreated samples that were normalized to 100%. The primers were used in the experiments

```
E15upF:
                                      (SEQ ID NO: 18)
5'-TCG GAG CGG TTG TGA ACT-3';

E15upR:
                                      (SEQ ID NO: 19)
5'-GTT CGC CGT TGT TCT GTC-3';

PabpF:
                                      (SEQ ID NO: 20)
5'-CTG CTG TTC ATG TGC AAG GT-3';

PabpR:
                                      (SEQ ID NO: 21)
5'-CAA CAG CAT GCC AGT GAT T-3'.
```

In Vitro Transcription of (CTG.CAG)$_{74}$ (SEQ ID NOS 3-4, respectively). T7 RNA polymerase-mediated transcription reactions were incubated at 37° C. for 2 h. A 10 µL mixture contained 15 ng of linearized plasmid (CTG)$_{74}$ (SEQ ID NO: 3) or control plasmid templates, 0.5 mM each rATP, rCTP, rGTP, and rUTP and 0.5 U T7 polymerase (Biolab) in 1×T7 transcription buffer (80 mM Tris pH 8.3, 10 mM MgCl$_2$, 2 mM spermine, 0.1% Triton-X, 10 mM NaCl). Ligand was added with the final concentrations of 0, 1, 10, 50, and 100 µM prior to incubation. Reactions were quenched by adding 8 µL of 8 M Urea and 2 µL of denaturing dye (95% formamide, 5 mM EDTA, 0.025% each xylene cyanol and bromophenol blue) and heating to 95° C. for 5 min. Of this solution, 15 µL was run on a 8% denaturing polyacrylamide gel in 0.5×TBE and stained with EtBr. Bands were quantified using the ImageJ (NIH). The intensity of (CUG)$_{74}$ (SEQ ID NO: 22) band (ca. 260 nt) was normalized to that from the untreated transcription reaction. The control plasmids were pTRI-Xefplasmid provided with MEGAscript® T7 transcription kit (Life Technologies) that expresses 1.89 kb RNA transcript and another non-repeat containing plasmid expressing a 197 nt RNA transcript.

Drug Treatment in *Drosophila*.

*Drosophila* lines were cultured in standard cornmeal medium supplemented with dry yeasts. Fly lines bearing UAS-(CTG)$_{60}$ (SEQ ID NO: 5) and UAS-(CTG)$_{480}$ (SEQ ID NO: 6) were kind gifts of Prof. Rubén Artero Allepuz (Universitat de València, Estudi General, Spain). The gmr-GAL4 and 24B-GAL4 lines were used to drive UAS transgene expression in eye and muscles respectively. Ligands 2 and 9 were dissolved in ddH$_2$O and mixed with fly food. Genetic crosses were set up in drug-containing fly food at 21.5° C. for external eye assay, and at 25° C. for larval crawling assay and real-time PCR analysis. For additional details see Wong et al., *J. Am. Chem. Soc.* 136, 6355-6361 (2014).

Larval Crawling Assay.

Larval crawling assays were performed as described in Lanson et al (*Hum. Mol. Genet.* 20, 2510-2523 (2011)). Ten wandering third instar larvae were washed in ddH$_2$O and placed on a 2% agarose gel in a 15-cm Petri dish with gridlines spaced at 0.5 cm. The larvae were allowed to acclimate for a period of 1 min, and the total number of gridlines that the posterior end of the larvae passed in 1 min was determined. Each set of experiment was repeated independently three times using larvae collected from separate genetic crosses.

RNA Extraction and Real-Time PCR.

RNA was extracted from third-instar larvae by TRIzol reagent (Invitrogen), and 1 µg of purified RNA was used for reverse transcription via the ImPromII Reverse Transcription System (Promega). Real-time PCR gene expression assays were performed on an ABI 7500 Real-time PCR system, using the SYBR® Green PCR Master Mix (ABI) with the following primers: SV40_F: 5'-GGA AAG TCC TTG GGG TCT TC-3' (SEQ ID NO: 23); SV40_R: 5'-GGA ACT GAT GAA TGG GAG CA-3' (SEQ ID NO: 24); actin_F: 5'-ATG TGC AAG GCC GGT TTC GC-3' (SEQ ID NO: 25) and actin_R: 5'-CGA CAC GCA GCT CAT TGT AG-3' (SEQ ID NO: 26). Each reaction was performed in duplicate. Quantification of gene expression was calculated according to the $2^{\Delta\Delta CT}$ method, where $\Delta\Delta C_T = (C_{T,\,target} - C_{T,\,actin})_{experimental} - (C_{T,\,target} - C_{T,\,actin})_{negative\,control}$. Each set of experiment was repeated independently for three times using larvae collected from separate genetic crosses.

Isothermal Titration Calorimetry.

Isothermal titration calorimetry (ITC) measurements were performed at 25° C. on a MicroCal VP-ITC (MicroCal, Inc., Northampton, Mass.). A standard experiment consisted of titrating 10 µL of a 500 µM ligand solution from a 250 µL syringe (rotating at 300 rpm) into a sample cell containing 1.42 mL of a 10 µM DNA or RNA solution. An ITC experiment consisted of 28 total injections (first injection was 5 µL, subsequent injections were 10 µL), with a 10 s duration per injection and delay of 380 s between injections. The initial delay prior to the first injection was 300 s. To derive the heat associated with each injection, the area under each isotherm (microcalories per second versus seconds) was determined by integration by the graphing program Origin 7.0 (MicroCal, Inc. Northampton, Mass.). The first data point from each ITC experiment was omitted when fitting to binding models due to possible diffusive mixing of material near the tip of the syringe. The fitting requirements were such that the thermodynamic parameters were derived from curves that produced the lowest amount of deviation. In most cases, fitting to a sequential site binding model-binding sites gave the most accurate data. The ligand stock solution was 10 mM in water. Double-stranded and hairpin DNA or RNA solutions were freshly prepared by mixing required volumes of the corresponding single stranded oligomers and annealing by heating in a water bath at >90° C. for 5 min and slowly cooling to room temperature. MOPS buffer solution (1 M), NaCl solution (5 M), and biological grade water were added to make up an oligonucleotide solution with 20 mM MOPS (pH 7.0±0.2), 300 mM NaCl.

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |

| (i) Tablet 1 | mg/tablet |
|---|---|
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X" | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

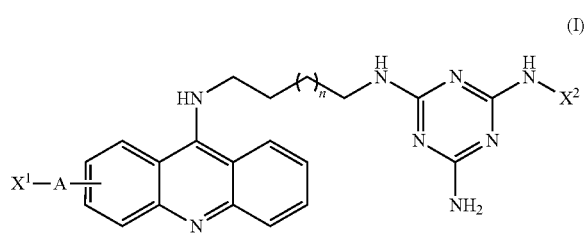

wherein n is 0, 1, or 2;

A is a direct bond or —C(=O)NH—;

$X^1$ and $X^2$ are each independently —H, —C(=O)NHCH$_2$CH$_2$N(CH$_2$CH$_2$NH$_2$)$_2$, or a moiety of Formula C1:

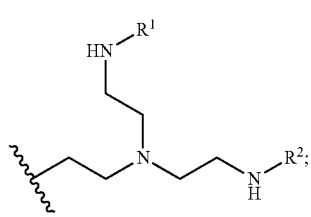

wherein $R^1$ and $R^2$ are each independently —H or a moiety of Formula C2:

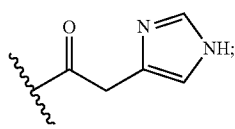

wherein at least one of $X^1$ and $X^2$ is not —H;

or a salt or solvate thereof.

2. The compound of claim 1 wherein $X^1$ is H.

3. The compound of claim 1 wherein $X^1$ is —C(=O)NHCH$_2$CH$_2$N(CH$_2$CH$_2$NH$_2$)$_2$.

4. The compound of claim 1 wherein $X^1$ is a moiety of Formula C1.

5. The compound of claim 4 wherein $R^1$ is H.

6. The compound of claim 4 wherein $R^1$ is a moiety of Formula C2.

7. The compound of claim 4 wherein $R^1$ and $R^2$ are each H.

8. The compound of claim 4 wherein $R^1$ and $R^2$ are each a moiety of Formula C2.

9. The compound of claim 4 wherein $R^1$ is H and $R^2$ is a moiety of Formula C2.

10. The compound of claim 1 wherein $X^2$ is H.

11. The compound of claim 1 wherein $X^2$ is —C(=O)NHCH$_2$CH$_2$N(CH$_2$CH$_2$NH$_2$)$_2$.

12. The compound of claim 1 wherein $X^2$ is a moiety of Formula C1.

13. The compound of claim 12 wherein $R^1$ is H.

14. The compound of claim 12 wherein $R^1$ is a moiety of Formula C2.

15. The compound of claim 12 wherein $R^1$ and $R^2$ are each H.

16. The compound of claim 12 wherein $R^1$ and $R^2$ are each a moiety of Formula C2.

17. The compound of claim 12 wherein $R^1$ is H and $R^2$ is a moiety of Formula C2.

18. A compound of Formula II:

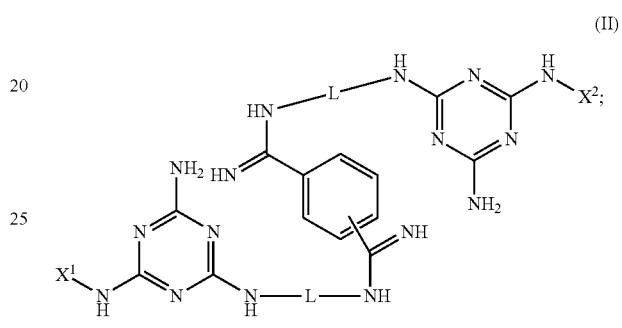

wherein each L is independently —(C$_3$-C$_5$)alkylene-, —(C$_2$-C$_5$)alkylene- interrupted by one oxygen, 1,3-cyclopenylene, 1,3-cyclohexylene, or 1,4-cyclohexylene;

$X^1$ and $X^2$ are each independently —H, —C(=O)NHCH$_2$CH$_2$N(CH$_2$CH$_2$NH$_2$)$_2$, or a moiety of Formula C1:

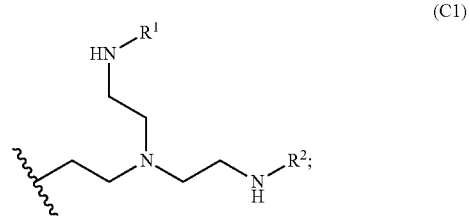

wherein $R^1$ and $R^2$ are each independently —H or a moiety of Formula C2:

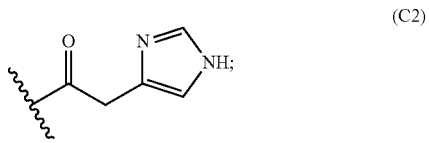 [SMILES: *C(=O)Cc1c[nH]cn1]

and wherein at least one of $X^1$ and $X^2$ is not —H;

or a salt or solvate thereof.

19. The compound:
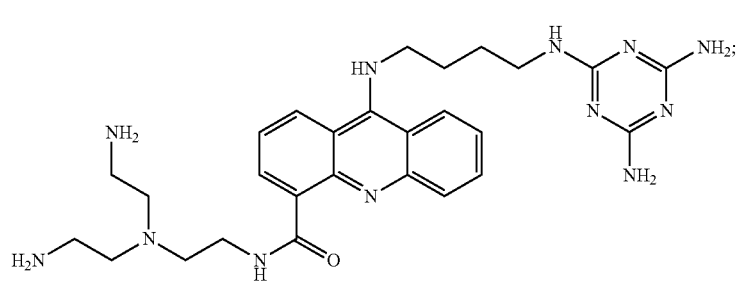
(4)
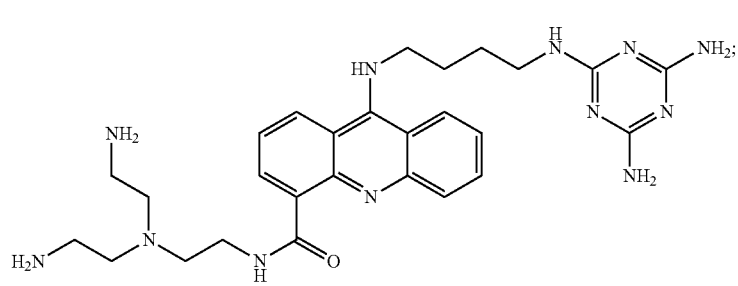
(5)
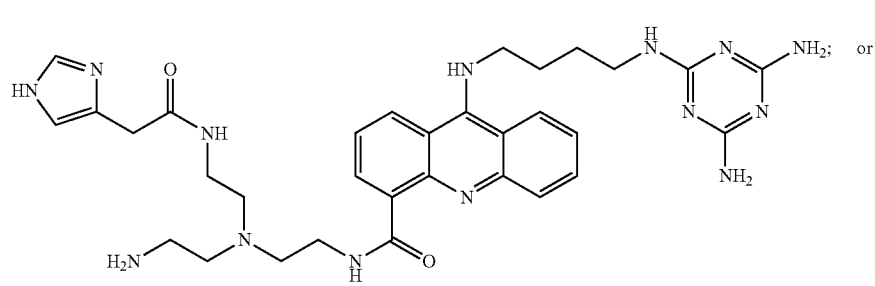
(6) or
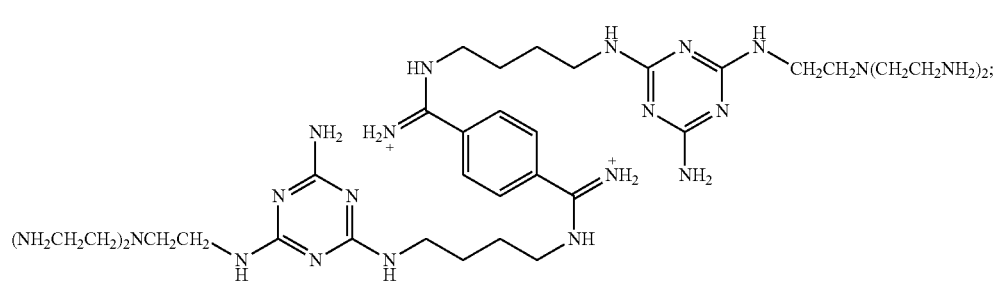
(9)
or a salt or solvate thereof.
20. A method of reducing the symptoms of myotonic dystrophy comprising administering to a patient having myotonic dystrophy an effective amount of a compound of claim 19, thereby reducing the symptoms of the myotonic dystrophy.
* * * * *